(12) United States Patent
Kabanov et al.

(10) Patent No.: US 6,696,089 B2
(45) Date of Patent: Feb. 24, 2004

(54) NANOGEL NETWORKS INCLUDING POLYION POLYMER FRAGMENTS AND BIOLOGICAL AGENT COMPOSITIONS THEREOF

(75) Inventors: Alexander V. Kabanov, Omaha, NE (US); Sergey V. Vinogradov, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 10/029,682

(22) Filed: Dec. 21, 2001

(65) Prior Publication Data

US 2002/0136769 A1 Sep. 26, 2002

Related U.S. Application Data

(63) Continuation-in-part of application No. 09/146,651, filed on Sep. 3, 1998, now Pat. No. 6,333,051.

(51) Int. Cl.$^7$ .......................... A61K 9/14; A61K 33/00; C08J 5/20; C08K 3/20; C08F 132/00
(52) U.S. Cl. .................. 424/484; 424/1.85; 424/130.1; 424/600; 424/486; 521/25; 523/404; 523/414; 514/1; 514/2; 514/44; 525/326.1
(58) Field of Search ............................... 424/484, 1.65, 424/130.1, 600, 486; 521/25; 523/404, 414; 514/1, 2, 44; 525/326.1

(56) References Cited

U.S. PATENT DOCUMENTS

| | | | |
|---|---|---|---|
| 4,059,552 A | | 11/1977 | Zweigle et al. |
| 4,172,066 A | | 10/1979 | Zweigle et al. |
| 4,189,539 A | * | 2/1980 | Ward et al. ................... 521/25 |
| 4,227,982 A | * | 10/1980 | Sekmakas et al. .......... 204/181 |
| 4,420,574 A | | 12/1983 | Moriarity et al. |
| 4,433,078 A | | 2/1984 | Kersten et al. |
| 4,560,714 A | | 12/1985 | Gajria et al. |
| 4,722,865 A | | 2/1988 | Huizer |
| 4,788,246 A | | 11/1988 | Tsuchiya et al. |
| 4,869,796 A | | 9/1989 | Kanda et al. |
| 5,280,078 A | * | 1/1994 | Gregor et al. ........... 525/328.5 |
| 5,300,541 A | | 4/1994 | Nugent, Jr. et al. |
| 5,529,777 A | | 6/1996 | Andrianov et al. |
| 5,545,423 A | | 8/1996 | Soon-Shiong et al. |
| 5,578,442 A | | 11/1996 | Desai et al. |
| 5,589,466 A | | 12/1996 | Felgner et al. |
| 5,593,658 A | * | 1/1997 | Bogdanov et al. .......... 424/9.34 |
| 5,714,166 A | * | 2/1998 | Tomalia et al. ............. 424/486 |

FOREIGN PATENT DOCUMENTS

| | | |
|---|---|---|
| EP | 0 030 885 A2 | 12/1979 |
| EP | 0 388 758 A1 | 3/1989 |
| EP | 0 544 292 A2 | 11/1992 |
| WO | WO 96/00295 | 6/1995 |

OTHER PUBLICATIONS

Rita Cortesi, et al.; Gelatin Microspheres as a New Approach for the Controlled Delivery of Synthetic Oligonucleotides and PCR–generated DNA Fragments; 1994; pp. 181–186; International Journal of Pharmaceutics 105.

Rosa Azhari, et al.; Protein Release from Enzymatically–Degradable Chondroitin–Sulfate/Gelatin Microspheres; 1991; pp. 617–618; Proceed. Intern. Symp. Control. Rel. Bioact. Mater. 18.

Paul T. Golumbek, et al.; Controlled Release, Biodegradable Cytokine Depots: A New Approach in Cancer Vaccine Design; 1993; pp. 5841–5844; Cancer Research 53.

H.C. Loughrey, et al.; Optimized Procedures for the Coupling of Proteins to Liposomes; 1990; pp. 25–35; Journal of Immunological Methods 132.

R. Azhari, et al.; Enzymatically–Triggered Release of Recombinant Soluble Complement Receptor 1 (SCR1) from Chondroitin Sulfate/Gelatin Microspheres; 1992; pp. 152–153; Proceed. Intern. Symp. Control. Rel. Bioact. Mater. 19; Controlled Release Society, Inc.

C. Nastruzzi, et al.; Production and In Vitro Evaluation of Gelatin Microspheres Containing an Antitumor Tetra–Amidine; 1994; pp. 249–260; J. Microencapsulation, vol. 11 No. 3.

* cited by examiner

*Primary Examiner*—Jezia Riley
(74) *Attorney, Agent, or Firm*—Mathews, Collins, Shepherd & McKay, P.A.

(57) ABSTRACT

The present invention relates to nanogel networks having at least one cross-linked polyionic polymer fragment and at least one nonionic water-soluble polymer fragment, and compositions thereof, having at least one suitable biological agent.

22 Claims, No Drawings

US 6,696,089 B2

NANOGEL NETWORKS INCLUDING POLYION POLYMER FRAGMENTS AND BIOLOGICAL AGENT COMPOSITIONS THEREOF

This is a continuation-in-part of Ser. No. 09/146,651 filed Sep. 3, 1998 now U.S. Pat. No. 6,333,051.

FIELD OF THE INVENTION

The invention relates to polymer technology, specifically polymer networks having at least one cross-linked polyion polymer fragment, in particular a polyanion, and at least one nonionic water-soluble polymer fragment, and compositions thereof.

BACKGROUND OF THE INVENTION

Conventional methods for the design of new drugs can be extremely difficult and time-consuming. For a new drug to be effective, it must be precisely matched to its molecular target. Moreover, once such a molecule is discovered, the new drug candidate must be soluble, bioavailable, nontoxic, and resistant to metabolic enzymes. Modifications to such a new molecule, necessary to satisfy these requirements, often have an adverse effect on the drug's therapeutic efficacy. Because of these complexities, conventional drug design can be a very costly, time-consuming process.

Recent advances in combinatorial chemistry technology have attempted to address these difficulties, however the problem of making such molecules soluble, bioavailable, resistant to metabolic enzymes, and capable of penetrating through membranes often remains unsolved.

The drug delivery industry has addressed some of these problems by incorporating drugs into carriers. In drug delivery assisted products, the time of development is somewhat shortened to approximately seven years, and the average cost is decreased. Unfortunately, many drug delivery systems still have several serious limitations in view of the problems discussed above.

SUMMARY OF THE INVENTION

The invention relates to copolymer networks having at least one cross-linked polyion polymer fragment and at least one nonionic water-soluble polymer fragment. These networks are in the nanometer size range. The copolymer networks are referred to as "nanogels".

This invention further relates to compositions of the nanogel networks of cross-linked polymer fragments of nanometer size range in which the nonionic water-soluble fragments contain hydrophilic and hydrophobic chain segments. The chain segments self assemble in an aqueous environment within the nanogel network volume resulting in formation of hydrophobic domains in each nanogel species that can incorporate and release nonpolar molecules or polar molecules containing non-polar parts. The aggregation of the nanogels through hydrophobic interactions between individual nanogels particles resulting in a formation of a precipitate or a bulk structure, such as a bulk gel, is undesirable. Accordingly, it is preferred that nanogels form stable dispersions.

This invention further relates to compositions having nanogel networks of cross-linked polymer fragments (defined herein as "polymer networks") and a suitable biological agent or agents.

The invention also relates to combinatorial drug delivery, or combinatorial formulation. The invention reduces the time and cost required for creating desired drug compounds, which are not only immediately ready for clinical trial, but also possess a number of important characteristics increasing the probability of ultimate success. In contrast to combinatorial chemistry, however, the invention does not discover new drug structures per se or alter the desirable drug characteristics themselves, but instead provides optimal compositions of a desired drug solving the drug's problems relating to solubility, bioavailability, resistance to metabolic enzymes, toxicity, membrane transport, and site specific delivery. Using a biological agent molecule as a starting point, the invention identifies new compositions with characteristics sought for the optimal performance of the selected molecule.

DETAILED DESCRIPTION

The invention thus relates to new chemical molecules having polymer networks of cross-linked polyion polymer fragments and nonionic polymer fragments. The dispersed polymer networks combine the properties of both polymer gels and colloidal particles. Polymer networks can contain both low molecular mass and polymer biological agents including, small molecules, oligo- and polysaccharides, polypeptides and proteins, polynucleotides such as RNA or DNA, and the like.

The invention also provides a method of identifying a biological agent composition of choice to create a cross-linked polymer network composition that will render a biological agent soluble, bioavailable, resistant to metabolic enzymes, non-toxic, freely traveling through membranes and into cells, or having desired release characteristics in the body. By using polymer networks which differ in the length and polymer fragment structure, and preparing composition corresponding libraries, the invention provides for rapid complexing and identification of compositions of biological agents with desired properties.

The invention further relates to biological compositions having polymer networks and biological agents. Dispersed polymer networks are capable of being transported in the body to a disease site, crossing biological barriers (such as the blood-brain barrier, and intestinal epithelium), entering cells, crossing cell membranes, and being transported to a target site inside a cell. These polymer network particles can be physically or chemically coupled with targeting molecules providing for site-specific delivery and recognition in the body.

The use of polymer fragments with dual functionality in polymer networks, such as polyionic polymers and nonionic water-soluble or water-swellable polymers, permits great variation in the properties of these systems by varying the lengths and/or chemical structure of the polymer fragments. This design of polymer network carriers provides for tremendous versatility with simple chemical structures and permits optimized drug delivery and drug release for enhanced performance with a variety of drugs and drug delivery applications. Particularly, (i) the longevity of circulation in the blood can be varied, (ii) biodistribution in the body can be varied to achieve site-specific drug delivery and release, and (iii) the rate of release can be varied (seconds, days, weeks, etc.). This versatility of the polymer networks permits selection of drug compositions that are most efficient and safe (i.e., have the best "therapeutic index") for a very broad variety of drugs.

This invention also provides for a method of identifying cross-linked polymer network and biological agent compositions that can be applied to pharmaceutics and biopharmaceutics diagnostics and imaging, immunology, veterinary, agriculture, and other areas where the properties of biological agents exhibited during interaction with a living organism or cell can be improved through formulation.

Biological agents suitable for use in accordance with the invention include agents useful for diagnostics or imaging, or that can act on a cell, organ or organism to create a change in the functioning of the cell, organ or organism. This includes, but is not limited to pharmaceutical agents, genes, vaccines, herbicides and the like.

The invention can be used in combination with high throughput screening of actual composition libraries, and can further utilize mathematical concepts, which have been found to be beneficial in combinatorial chemistry.

Definitions

As used herein, the terms below have the following meaning:

| | |
|---|---|
| Backbone: | Used in graft copolymer nomenclature to describe the chain onto which the graft is formed. |
| Biological agent: | An agent that is useful for diagnosing or imaging or that can act on a cell, organ or organism, including but not limited to drugs (pharmaceuticals) to create a change in the functioning of the cell, organ or organism. |
| Biological property: | Any property of biological agent or biological agent composition that affects the action of this biological agent or biological agent composition during interaction with a biological system. |
| Block copolymer: | A combination of two or more chains of constitutionally or configurationally different features linked in a linear fashion. |
| Branched polymer: | A combination of two or more chains linked to each other, in which the end of at least one chain is bonded at some point along the other chain. |
| Chain: | A polymer molecule formed by covalent linking of monomeric units. |
| Composition library: | A Plurality of compositions of biological agents with polymer networks. |
| Configuration: | Organization of atoms along the polymer chain, which can be interconverted only by the breakage and reformation of primary chemical bonds. |
| Conformation: | Arrangements of atoms and substituents of the polymer chain brought about by rotations about single bonds. |
| Conterminous: | At both ends or at points along the chain. |
| Conterminous link: | A polymer cross-link in which a polymer chain is linked at both ends to the same or constitutionally or configurationally different chain or chains. |
| Copolymer: | A polymer that is derived from more than one species of monomer. |
| Cross-link: | A structure bonding two or more polymer chains together. |
| Dendrimer: | A regularly branched polymer in which branches start from one or more centers. |
| Dispersion: | Particulate matter distributed throughout a continuous medium. |
| Drug candidate: | A substance with biological activity potentially useful for therapy. |
| Interpenetrating network: | An intimate combination of at least two polymer networks at least one of which is synthesized in the immediate presence of the other. |
| Graft copolymer: | A combination of two or more chains of constitutionally or configurationally different features, one of which serves as a backbone main chain, and at least one of which is bonded at some points along the backbone and constitutes a side chain. |

-continued

| | |
|---|---|
| Homopolymer: | Polymer that is derived from one species of monomer. |
| Link: | A covalent chemical bond between two atoms, including bond between two monomeric units, or between two polymer chains. |
| Nanogel: | A polymer network dispersion with sub-micron particle size. |
| Network: | A three-dimensional polymer structure, where all the chains are connected through cross-links. |
| Network basis: | plurality of cross-linked polymer networks differing in at least one of the polymer fragment constitutional, configurational or conformational feature. |
| Parent database: | Computer database containing information on known polymer networks. |
| Polyanion: | A polymer chain containing repeating units containing groups capable of ionization in aqueous solution resulting in formation of a negative charges on the polymer chain. |
| Polycation: | A polymer chain containing repeating units containing groups capable of ionization in aqueous solution resulting in formation of a positive charges on the polymer chain. |
| Polyion: | A polymer chain containing repeating units containing groups capable of ionization in aqueous solution resulting in formation of a positive or negative charges on the polymer chain. |
| Polymer blend: | An intimate combination of two or more polymer chains of constitutionally or configurationally different features, which are not bonded to each other. |
| Polymer fragment: | A portion of polymer molecule in which the monomeric units have at least one constitutional or configurational feature absent from adjacent portions. |
| Repeating unit: | Monomeric unit linked into a polymer chain. |
| Semi-interpenetrating: | Used herein to describe an intimate combination of at least one non cross-linked polymer and at least one polymer network at least one of which is synthesized in the immediate presence of the other. |
| Side chain: | The grafted chain in a graft copolymer. |
| Starblock copolymer: | Three or more chains of different constitutional or configurational features linked together at one end through a central moiety. |
| Star polymer: | Three or more chains linked together at one end through a central moiety. |
| Surfactant: | Surface active agent that is adsorbed at interface. |
| Virtual library: | A list of polymer networks potentially useful with the biological agent. |
| Viral Vector: | A construct derived from a virus and used in gene transfer. |

The invention relates to networks of cross-linked polymer fragments wherein the fragments comprise:
(a) at least one polyanion fragment comprising at least three of the same or different repeating units each capable of ionization resulting in formation of negative charge in aqueous solution; and
(b) at least one nonionic homopolymer or copolymer comprising at least three of the same or different repeating units containing at least one atom selected from the group consisting of oxygen and nitrogen.

The invention provides fine dispersions of the networks with a sub-micron range of particle size ("nanogels").

This invention further relates to compositions of the nanogel networks of cross-linked polymer fragments of nanometer size range in which the nonionic water-soluble fragments contain hydrophilic and hydrophobic chain segments. The chain segments self assemble in an aqueous environment within the nanogel network volume resulting in formation of hydrophobic domains in each nanogel species that can incorporate and release nonpolar molecules or polar molecules containing significant non-polar parts. The aggregation of the nanogels through hydrophobic interactions between individual nanogels particles resulting in a formation of a precipitate or a bulk structure, such as a bulk gel, is undesirable. It is preferred that nanogels form stable dispersions. The preferred range of the size of nanogel networks is from about 20 nm to about 300 nm, more preferred from about 20 nm to about 200 nm, still more preferred from about 20 nm to about 100 nm, still more preferred from about 20 nm to about 50 nm.

This invention further relates to compositions having the nanogel networks of cross-linked polymer fragments (defined herein as "polymer networks") and at least one suitable biological agent. The biological agents are incorporated into nanogel particles through hydrophobic, ionic interactions or hydrogen bonding. In the case of biological agents bearing one or several electrostatic charges it is preferred that the net charge of such molecule is opposite to the charge of the nanogel, i.e. be positive (or cationic).

The polyion, polyanion, polycation and nonionic polymer fragments independently of each other can be linear polymers, randomly branched polymers, block copolymers, graft copolymers, star polymers, star block copolymers, dendrimers or have other architectures, including combinations of the above-listed structures. The degree of polymerization of the polyion and nonionic polymer fragments is between about 20 and about 100,000. More preferably, the degree of polymerization is between about 30 and about 10,000, still more preferably, between about 30 and about 1,000.

Preferred polyanion fragments, which form the polymer networks, comprise at least three of the same or different repeating units containing at least one atom selected from the group consisting of oxygen, sulfur, or phosphorus. Suitable polyanion fragments are homopolymers or copolymers and the salts thereof which include repeating units containing carboxylic, sulfonic, sulfuric, phosphoric, or the salts thereof, such carboxylates, sulfonates, sulfates, phosphates, phosphonates and the like have been described in March, "Advanced Organic Chemistry", 4th edition, 1992, Wiley-Interscience, New York.

Example polyanion segments include but are not limited to polymethacrylic acid and its salts; polyacrylic acid and its salts; copolymers of methacrylic acids and its salts; copolymers of acrylic acid and its salts; heparin; poly(phosphate); polyamino acid, such as polyaspartic acid, polylactic acid, and their copolymers, polynucleotides, carboxylated dextran, and the like. Preferred polyanions include the products of polymerization or copolymerization of monomers that polymerize to yield a product having carboyl pendant groups. Representative examples of such monomers are acrylic acid, aspartic acid, 1,4-phenylenediacrylic acid, citracinic acid, citraconic anhydride, trans-cinnamic acid, 4-hydroxy cinnamic acid, trans-glutaconic acid, glutamic acid, itaconic acid, linoleic acid, linolenic acid, methacrylic acid, trans-beta-hydromuconic acid, trans—trans-muconic acid, ricinolei acid, 2-propene-1-sulfonic acid, 4-styrene sulfonic acid, trans-traumatic acid, vinylsulfonic acid, vinyl phosphoric acid, vinyl benzoic acid and vinyl glycolic acid. The polyanion fragments have several ionizable groups that can form net negative charge at physiologic pH. Preferably, the polyanion fragments will have at least about 3 negative charges at physiologic pH, more preferably, at 25 least about 6, still more preferably, at least about 12. Also preferred are polymers or fragments that, at physiologic pH, can present negative charges with about a distances between the charges of about 2 Å to about 10 Å.

It is preferred that nonionic polymer fragments comprise water-soluble polymers, which are nontoxic and nonimmunogenic. The preferred nonionic polymer fragment is a polyethylene oxide, a copolymer of ethylene oxide and propylene oxide, a polysaccharide, a polyacrylamide, a polyglycerol, a polyvinylalcohol, a polyvinyl-pyrrolidone, a polyvinylpyridine N-oxide, a copolymer of vinylpyridine N-oxide and vinylpyridine, a polyoxazoline, or a polyacroylmorpholine or the derivatives thereof, in which the number of repeating units has a value of from 3 to about 50,000,000.

In one preferred embodiment of the present invention the nonionic fragments contain hydrophilic and hydrophobic chain segments. An example of such nonionic polymer nonionic polymer fragments are the block copolymers of ethylene oxide and propylene oxide having the formulas:

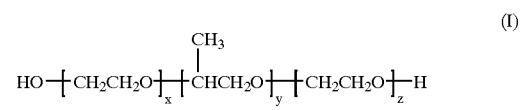

(I)

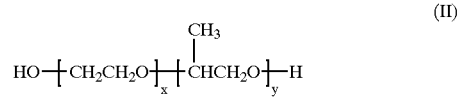

(II)

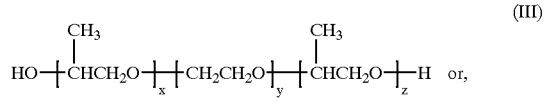

(III)

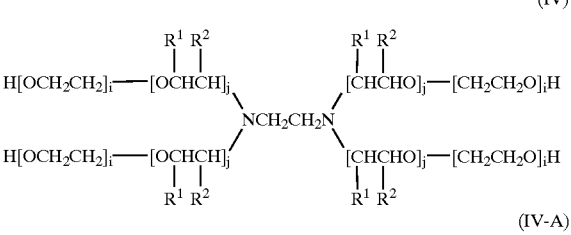

(IV)

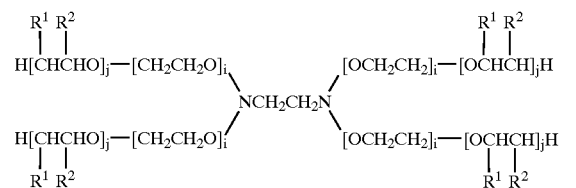

(IV-A)

in which x, y, z, i and j have values from about 2 to about 800, preferably from about 5 to about 200, more preferably from about 5 to about 80, and wherein for each $R^1$, $R^2$ pair, one is hydrogen and the other is a methyl group.

Formulas (I) through (III) are oversimplified in that, in practice, the orientation of the isopropylene radicals within the poly(oxypropylene) block can be random or regular. This is indicated in formula (IV), which is more complete. Such poly(oxyethylene)-poly(oxypropylene) compounds have been described by Santon, *Am. Perfumer Cosmet.* 72(4):54–58 (1958); Schmolka, *Loc. cit.* 82(7):25 (1967); Schick, *Non-ionic Surfactants*, pp. 300–371 (Dekker, N.Y., 1967). A number of such compounds are commercially available under such generic trade names as "poloxamers", "pluronics" and "synperonics." Pluronic polymers within the B-A-B formula are often referred to as "reversed" pluronics, "pluronic R" or "meroxapol". The "polyoxamine" polymer of formula (IV) is available from BASF (Wyandotte, Mich.) under the tradename Tetronic™. The order of the polyoxyethylene and polyoxypropylene blocks represented in formula (XVII) can be reversed, creating Tetronic R™, also available from BASF. See, Schmolka, *J. Am. Oil Soc.*, 59:110 (1979). Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available from BASF under the tradename Pluradot™.

The diamine-linked pluronic of formula (IV) can also be a member of the family of diamine-linked polyoxyethylene-polyoxypropylene polymers of formula:

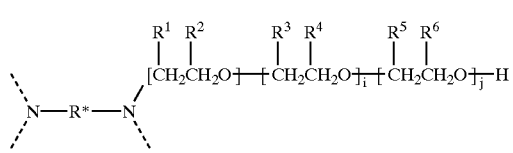

(V)

wherein the dashed lines represent symmetrical copies of the polyether extending off the second nitrogen, $R^*$ is an alkylene of 2 to 6 carbons, a cycloalkylene of 5 to 8 carbons or phenylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, if both of $R^3$ and $R^4$ are hydrogen, then one $R^5$ and $R^6$ is hydrogen and the other is methyl, and if one of $R^3$ and $R^4$ is methyl, then both of $R^5$ and $R^6$ are hydrogen.

Those of ordinary skill in the art will recognize, in light of the discussion herein, that even when the practice of the invention is confined for example, to poly(oxyethylene)-poly(oxypropylene) compounds, the above exemplary formulas are too confining. Thus, the units making up the first block need not consist solely of ethylene oxide. Similarly, not all of the second type block need consist solely of propylene oxide units. Instead, the blocks can incorporate monomers other than those defined in formulas (I)–(V), so long as the parameters of this first embodiment are maintained. Thus, in the simplest of examples, at least one of the monomers in hydrophilic block might be substituted with a side chain group as previously described.

The term "link" used herein means covalent bond between two atoms, including bonds between two monomeric units, or between two polymer chains. The term "cross-link" as used herein refers to a structure bonding two or more polymer chains together. The polymer network of the current invention can be produced by covalent linkage of one polymer fragment to at least two other polymer fragments having the same or different structure. The linkage of the polymer fragments in the networks can be conterminous, i.e., a polymer cross-link in which a polymer chain is linked at both ends to the same or constitutionally or configurationally different chain or chains. The conterminous polymer networks can be produced by covalently cross-linking the polyion fragments by nonionic fragments or pendant groups or vice versa cross-linking the nonionic fragments by the polyion fragments. For example, the polymer networks can be synthesized by reacting polyoxyethylene having reactive groups at two ends, such as polyoxyethylene bis-amine, with carboxylic groups of poly(acrylic acid). Another example, is linking periodate oxidized carboxymethyl polymers through polyoxyethylene bis-amine. The network can also be obtained by cross-linking the pendant groups of polymer fragments. For example, linking the pendant carboxylic groups poly(acrylic acid) or poly(glutamic acid) to polyvinylalcohol chains having activated pendant hydroxyl groups through the cross-linking agents can produce such network. The networks can also combine conterminous and non-conterminous linkage. Without wishing to be limited to any one particular theory, it is believed that the polymer networks of the current invention can also be interpenetrating or semi-interpenetrating, and can non-covalently trap polymers and other molecules present during their synthesis. Those of ordinary skill in the art will recognize that numerous types of the polymer network architecture described in the literature can be utilized in accordance with the current invention. See for example, Sperling, Introduction to Physical Polymer Science, 2d Ed., Johen Wiley, New York, 1992.

Polymer gels can be synthesized by free radical UV co-polymerization of the high molecular nonionic monomers that form polyanionic network in the presence of other nonionic and/or polyanionic fragments. For example, nanoparticles were prepared from poly(ethylene glycol) monomethyl ether monomethacrylate, tetraethylene glycol dimethacrylate and either methacrylic or acrylic acid. See Foss et al., Polym. Prepr. 42(2), 94 (2001), Ward et al., J. Contr. Release 71(2), 183 (2001), Nakamura et al., J. Contr. Release 61(3), 329 (1999). Cationic microgel dispersions can be produced by cross-linking polyepoxide-amine reaction products with polyepoxide cross-linking agent, see U.S. Pat. No. 5,096,556. Polymerizing epoxides with polyalkylenepolyamines produced polymer beads, see U.S. Pat. No. 4,189,539. Certain carboxylic acid containing microgel particles can be prepared by polymerizing in aqueous emulsion a monomer mixture containing carboxylic acid monomers and vinyl monomers (see U.S. Pat. No. 4,560,714).

Another approach to synthesizing polymer networks was used to obtain bioadhesive lattices of water-swollen poly (acrylic acid) nano- and microparticles. The inverse (W/O) emulsion polymerization occurred in the presence of radical initiators, such as azobis-isobutyronitrile, See Kriwet et al., J. Contr. Release 56(1–3), 149 (1998).

Polymer micelles could be cross-linked to stabilize forming core-shell nanospheres. Cross linking can be accomplished by direct reaction between the chain segments located within the polymer micelle shell, or via addition of multi-functional cross linking reagents. See Thurmond et al., Colloids Surf., B, 16(1–4), 45 (1999).

A hydrogel network can be formed by mixing two oppositely charged polymer molecules. For example, solutions of dextran sulfate and polyethylenimine at mass ratio 0.3–0.7 produced nanoparticles. See PCT Int. Appl. (2001), WO 2001001964. Alternatively, polymers can be linked into a network using a covalent bond.

Linking of polymers and polymer fragments can be accomplished by a number of reactions, many of which have been described generally in conjugate chemistry, in particular, for synthesizing block and graft copolymers, and various polymer conjugates. See for example, Seymour et al., Self-Assembling Complexes for Gene Delivery. From Laboratory to Clinical Trial, Kabanov et al. (eds.), John Wiley, Chichester (1998); U.S. Pat. Nos. 5,593,658, 5,567, 410, and 5,656,611. These reactions can involve, for example, a terminal or pendant hydroxyl group on one polymer fragment, e.g. $R^5$—O—$(C_2H_4O)$—H, in which $R^5$ is hydrogen or a blocking group such as alkyl, and an appropriate group on another polymer fragment, the two being joined directly or indirectly; i.e., through a third component. Alternatively a terminal or pendant group can be converted to some other functional group, such as an amino group, which then is allowed to react with either the next polymer fragment or another linking component. The linking group thus may be formed either by reactively involving a terminal or pendant group of a polymer fragment or by replacing the terminal or pendant group. For example, a carboxylic acid group can be activated with N,N'-dicyclohexylcarbodiimide and then allowed to react with an amino or hydroxy group to form an amide or ether respectively. Anhydrides and acid chlorides will produce the same links with amines and alcohols. Alcohols can be activated by carbonyldiimidazole and then linked to amines to produce urethane linkages or activated to produce ethers or esters. Alkyl halides can be converted to amines or allowed to react with an amine, diamines, alcohols, or diol. A terminal or pendant hydroxy group can be oxidized to form the corresponding aldehyde or ketone. This aldehyde or ketone then is allowed to react with a precursor carrying a terminal or pendant amino group to form an imine which, in turn, is reduced, with sodium borohydrate to form the secondary amine. See Kabanov et al., *J. Contr. Release*, 22:141 (1992); *Meth. Enzymol.*, XLVII, Hirs & Timasheff, Eds., Acad. Press, 1977. The linkage thereby formed is the group —NH—, replacing the terminal or pendant hydroxyl group of the polymer fragment.

Alternatively, a terminal or pendant hydroxyl group on the polymer can be reacted with bromoacetyl chloride to form a bromoacetyl ester which in turn is reacted with an amine precursor to form the —NH—$CH_2$—C(O)— linkage. See Immobilized Enzymes, Berezin et al. (eds.), MGU, Moscow, 1976 (—NH—$CH_2$—C(O)—). The bromoacetyl ester of a polymer fragment also can be reacted with a diaminoalkane of the formula $NH_2$—$C_qH_{2q}$—$NH_2$ which in turn is reacted with an carboxy group on another polymer fragment, or an activated derivative thereof such as an acid chloride or anhydride. The bromoacetyl ester also can be reacted with a cyanide salt to form a cyano intermediate. See e.g., Sekiguchi et al., *J. Biochem.*, 85, 75 (1979); Tuengler et al., *Biochem. Biophys. Acta*, 484, 1 (1977); Browne et al. BBRC, 67, 126 (1975); and Hunter et al., JACS 84, 3491 (1962). This cyano intermediate then can be converted to an imido ester, for instance by treatment with a solution of methanol and hydrogen chloride, which is reacted with an amine precursor to form a —NH—C($NH_2^+$)$CH_2$C(O)— linkage. A terminal or pendant hydroxyl group also can be reacted with 1,1'-carbonyl-bis-imidazole and this intermediate in turn reacted with an amino precursor to form a —NH—C(O)O— linkage. See Bartling et al., Nature 243, 342 (1973).

A terminal or pendant hydroxyl also can be reacted with a cyclic anhydride such as succinic anhydride to yield a half-ester which, in turn, is reacted with a precursor having terminal or pendant amino group using conventional condensation techniques for forming peptide bonds such as dicyclohexylcarbodiimide, diphenylchlorophosphonate, or 2-chloro-4,6-dimethoxy-1,3,5-triazine. See e.g., Means et al., Chemical Modification of Proteins, Holden-Day (1971). Thus formed is the —NHC(O)($CH_2$)$_q$C(O)O— linkage.

A terminal or pendant hydroxyl group also can be reacted with 1,4-butanediol diglycidyl ether to form an intermediate having a terminal or pendant epoxide function linked to the polymer through an ether bond. The terminal or pendant epoxide function, in turn, is then reacted with an amino precursor. Pitha et al., *Eur. J. Biochem.*, 94:11 (1979); Elling and Kula, *Biotech. Appl. Biochem.*, 13:354 (1991); Stark and Holmberg, *Biotech. Bioeng.*, 34:942 (1989).

Halogenation of a terminal or pendant hydroxyl group permits subsequent reaction with an alkanediamine such as 1,6-hexanediamine. The resulting product then is reacted with carbon disulfide in the presence of potassium hydroxide, followed by the addition of proprionyl chloride to generate a isothiocyanate which in turn is reacted with an amino precursor to yield a —N—C(S)—N—($CH_2$)$_6$—NH— linkage. See Means et al., Chemical Modification of Proteins, Holden-Day (1971). The polymer chain terminating in an amino group also can be treated with phosgene and then another polymer fragment containing amino group to form an urea linkage. See Means et al., Chemical Modification of Proteins, Holden-Day (1971).

The polymer fragment terminating in an amino group also can be treated with dimethyl ester of an alkane dicarboxylic acid and the product reacted with an amino precursor to produce a —N—C($NH_2^+$)—($CH_2$)$_4$—C($NH_2^+$)—N— linkage. See Lowe et al., Affinity Chromatography, Wiley & Sons (1974). The polymer fragment terminating in an amino group also can be reacted with an alkanoic acid or fluorinated alkanoic acid, preferably an activated derivative thereof such as an acid chloride or anhydride, to form a linking group, —CONH—. Alternatively an amino precursor can be treated with an α,ω-diisocyanoalkane to produce a —NC(O)NH($CH_2$)$_6$NHC(O)—N— linkage. See Means et al. Chemical Modification of Proteins, Holden-Day (1971). Some linking groups thus can simply involve a simple functional group while others may comprise a spacer unit such as a polymethylene chain between two functional groups. When the linking group comprises such a polymethylene chain, it can have as few as two methylene units but preferably contains more; e.g., six or more methylene units. The above descriptions exemplify typical strategies for the formation of linkages between the fragments of the polymer networks of the current invention. These procedures parallel those, which are known to form conjugates of biologically active agents and other agents, including the general conjugation methods described by Means et al., Chemical Modification of Proteins, Holden-Day (1971); Glazer et al., Chemical Modification of Proteins, Elsevier, New York (1975); Immunotechnology Catalog & Handbook, Pierce Chemical Co.; and Polyethylene Glycol Derivatives Catalog, Shearwater Polymers, Inc. (1994). It will also be appreciated that linkages which are not symmetrical, such as —CONH— or —NHCOO—, can be present in the reverse orientation; e.g., —NHCO— and —OCONH—, respectively.

The size of the polymer networks is one major parameter determining their usefulness in biological compositions. After administration in the body large particles are eliminated by the reticuloendothelial system and cannot be easily transported to the disease site (see, for example, Kabanov et al., *J. Contr. Release*, 22, 141 (1992); Volkheimer. Pathologe 14:247 (1993); Kwon and Kataoka, *Adv. Drug. Del. Rev.* 16:295 (1995). Also, the transport of large particles in the cell and intracellular delivery is limited or insignificant. See, e.g., Labhasetwar et al. Adv. Drug Del. Res. 24:63 (1997). It was demonstrated that aggregated cationic species with a size from 500 nm to over 1 μm are ineffective in cell transfection, see Kabanov et al., Self-Assembling Complexes for Gene Delivery. *From Laboratory to Clinical Trial,* Kabanov et al. (eds.), John Wiley, Chichester (1998) and references cited. Large particles, particularly, those positively charged exhibit high toxicity in the body, in part due to adverse effects on liver and embolism. See e.g., Volkheimer, Pathologe 14:247 (1993); Khopade et al Pharmazie 51:558 (1996); Yamashita et al., *Vet. Hum. Toxicol.*, 39:71 (1997). Nanogel polymer networks are nontoxic, can enter into small capillaries in the body, transport in the body to a disease site, cross biological barriers (including but not limited to the blood-brain barrier and intestinal epithelium), absorb into cell endocytic vesicles, cross cell membranes and transport to the target site inside the cell. The particles in that size range are believed to be more efficiently transferred across the arterial wall compared to larger size microparticles, see Labhasetwar et al., *Adv. Drug Del. Res.* 24:63 (1997). Without wishing to be bound by any particular theory it is also believed that because of high surface to volume ratio, the small size is essential for successful targeting of such particles using targeting molecules. Further, it is also believed the nanogel size ranges are preferred for the optimal performance of the polymer networks in the combinatorial formulations. The preferred range of the size of nanogel networks is from about 20 nm to about 300 nm, more preferred from about 20 nm to about 200 nm, still more preferred from about 20 nm to about 100 nm, still more preferred from about 20 nm to about 50 nm.

While not wishing to be bound by any specific theory, it is further believed that nanogel particles shall have these sizes in a swollen state in aqueous solutions. As is shown in the examples, the sizes of the nanogels can decrease as the biologically active molecule incorporates in the nanogel particle.

It is also believed that maintaining the particle size distribution in the preferred range and thorough purification from larger particles is essential for the efficiency and safety of the nanogel networks. It is recognized that useful properties of the nanogel networks are determined solely by their size and structure and are independent of the method used for their preparation. Therefore, this invention is not limited to a certain synthesis or purification procedures, but rather encompasses new and novel chemical entities useful in biological agent compositions.

Those of ordinary skill in the art will recognize that even when the practice of the invention is confined, for example, to certain nanogel networks there are numerous methods of particle preparation and dispersion that will yield the nanogel networks with the desired characteristics. Thus, any method resulting in a nanogel species with the desired characteristics is suitable for preparation of the polymer networks and biological agent compositions thereof. Many such useful methods can be found in nanotechnologies and nanoparticle chemistry. See for example, Hrkach et al. Biomaterials, 18:27 (1997). Nanoparticles and nanospheres can be synthesized in aqueous and non-aqueous emulsions under the appropriate conditions and then separated by size exclusion chromatography, membrane filtration, ultracentrifugation or similar technique. See, for example, Bertling, et al., *Appl. Biochem.,* 13, 390 (1991); Lukowski et al., *Int. J. Pharm.,* 84, 23 (1992); Pirker et al., *Int. J. Pharm.,* 128, 189 (1996); Peracchia, et al. *J. Contr. Rel.,* 46, 223 (1997); Zobel et al. *Antisense Nucl. Acid Drug Dev.* 7, 483 (1997); Ferdous, et al. *J. Contr. Rel.* 50, 71 (1998); and literature cited. The "water-in-oil" and "oil-in-water" microemulsions as well as normal and reverse surfactant micelles have proven to be particularly useful for preparation of particles with the preferred size distribution. See, for example, Abakumova, et al., *Dokl. Acad. Nauk SSSR,* 283, 136 (1985); Khmelnitsky, et al., *Eur. J. Biochem.,* 210, 751 (1992). Methods of nanoparticle preparation include but are not limited to emulsification-solvent evaporation technique, multiple emulsion solvent evaporation technique, phase inversion, coacervation, salting out, spray drying, emulsion and micro-emulsion polymerization, and the like. See Labhasetwar, In Self-Assembling Complexes for Gene Delivery. From Laboratory to Clinical Trial, Kabanov et al. (eds.), John Wiley, Chichester (1998). By varying conditions of reaction, including the type and dispersity of the media, addition of surfactants, temperature, and ratio of reagents the size of the particles can be controlled.

Certain nanoparticles were recently proposed as carriers for certain pharmaceutical agents. See, e.g., Sharma et al. Oncology Research 8, 281 (1996); Zobel et al. Antisense Nucl. Acid Drug Dev., 7:483 (1997); de Verdiere et al. Br. J. Cancer 76, 198 (1997); Hussein et al., Pharm. Res., 14, 613 (1997); Alyautdin et al. Pharm. Res. 14, 325 (1997); Hrkach et al. Biomaterials, 18, 27 (1997); Torchilin, J. Microencapsulation 15, 1 (1988); Labhasetwar, Self-Assembling Complexes for Gene Delivery; *From Laboratory to Clinical Trial,* Kabanov et al. (eds.), John Wiley, Chichester (1998); and literature cited therein. The nanoparticle chemistries provide for a wide spectrum of rigid polymer structures, which are suitable for the encapsulation of drugs, drug delivery and controlled release. Some major problems of these carriers include aggregation, low drug loading capacity and restricted control of the drug release kinetics.

Due to their unique architecture, nanogel polymer networks combine properties of cross-linked polymer gels and dispersed colloidal particles. They are porous materials which can be loaded with a variety of biological agents, including small molecules and polymers, at a very high biological agent to polymer network ratio. The immobilization of the biological agents in the nanogel networks is in the entire volume of the network rather than on its surface, and under certain conditions can be accompanied by the micro-collapse of the network providing for additional masking and protection of the biological agent. Nanogel networks of the current invention are soluble and do not aggregate after complete neutralization of the polyion charges. The loading capacity of nanogel networks can be as high as several grams or several dozen grams per one gram of the polymer network. This is much higher compared to the loading capacity achieved with nanoparticles. See, Labhasetwar et al., Adv. Drug Del. Res., 24:63 (1997). In contrast to conventional drug delivery particles such as nanoparticles (which usually have to be prepared in the presence of the biological agent) the polymer network is loaded with the biological agent after the network its synthesized. This greatly simplifies the preparation and use of the biological agent composition of this invention and permits using batches of nanogel network with many different biological agents and compositions.

The combination of the polyion and nonionic fragments (including hydrophobic-hydrophilic block copolymers) enables formulation of the nanogel networks with a broader range of biological agents as compared to most other particulate drug delivery and controlled release systems. Combination of polyanion and nonionic polymer fragments in the polymer networks provides for much greater versatility and enhanced properties as compared with conventional drug delivery systems. Also this invention relates to compositions of the nanogel networks in which the nonionic water-soluble fragments contain hydrophilic and hydrophobic chain segments. Such segments self assemble in aqueous environment within the nanogel network resulting in formation of hydrophobic domains in each nanogel species that can incorporate and release nonpolar molecules or polar molecules containing non-polar parts. The ability to change the structure and porosity of nanogel networks by altering the polymer fragment structure is unprecedented for any particulate delivery system. Also, due to the small size the polymeric species can be transported in the body to a disease site, cross biological barriers including but not limited to the blood-brain barrier and intestinal epithelium, enter cells, cross cell membranes and be transported to the target site inside cell.

This invention further relates to compositions having the nanogel networks of cross-linked polymer fragments (defined herein as "polymer networks") and at least one suitable biological agent. The biological agents incorporate into nanogel particles through hydrophobic, ionic interactions or hydrogen bonding forming non-covalent complexes. It is preferred that there is a combination of binding interactions between the biological agent and nanogel, for example, ionic (electrostatic) and hydrophobic binding, or hydrogen bonding and hydrophobic binding, or ionic (electrostatic) and hydrogen bonding. The complexes are more stable and more suitable allowing their successful use in the body when the combination of interactions is present.

In the case of biological agents bearing one or several electrostatic charges it is preferred that the net charge of such agent is opposite to the charge of the nanogel, i.e. be positive (or cationic). The compositions of biological agents and nanogels include surfactant biological agents containing hydrophilic and hydrophobic parts. If the hydrophilic part is positively charged such structures are referred to as "the cationic surfactants".

Surfactants can cooperatively bind to the polymers of opposite charge (see, for example, Goddard, In *Interactions of Surfactants with Polymers and Proteins.* Goddard and Ananthapadmanabhan, Eds., pp. 171 et seq., CRC Press, Boca Raton, Ann Arbor, London, Tokyo, 1992). Cooperative binding occurs if the binding of surfactant molecules to the polymer is enhanced by the presence of other molecules of this or other surfactant, which are already bound to the same polymer. According to the present invention a surfactant binds electrostatically to oppositely charged anionic fragments of the nanogel to form complexes. These complexes are cooperatively stabilized by the interactions of the hydrophobic parts of surfactant molecules bound to the same anionic fragment with each other. This binding mechanism is, in particular, characteristic for surfactant biological agents, see, for example, Florence and Attwood, *Physicochemical Principles of Pharmacy,* $2^{nd}$ edn., p.180 et seq., Chapman and Hall, New York, 1988).

Formation of the electrostatic complexes between cationic surfactants and anionic polymer chains results in charge neutralization. As a result, hydrophobicity of the complexed fragments increases and aqueous solubility decreases. However, the preferred biological agent compositions remain in the aqueous solution due to the presence of the nonionic fragments linked to the anionic segments. By varying the relative lengths and amounts of the nonionic and polyionic fragments it is possible to vary the hydrophilic-lipophilic properties of the complexes formed between the surfactant and nanogel and to optimize the stability of the preferred compositions in the dispersions. It is preferred that the compositions of the present invention form stable aqueous dispersions at physiological conditions (pH, osmomolarity, etc.) and temperatures.

It will in some circumstances be desirable to incorporate in the nanogel networks of the current invention, by non-covalent association or covalent conjugation, targeting molecules. See for example, Kabanov et al., *J. Controlled Release,* 22:141 (1992), the contents of which are hereby incorporated by reference. As used herein, the term "targeting molecule" refers to any molecule, atom, or ion linked to the polymer networks of the current invention that enhance binding, transport, accumulation, residence time, bioavailability or modify biological activity of the polymer networks or biologically active compositions of the current invention in the body or cell. The targeting molecule will frequently comprise an antibody, fragment of antibody or chimeric antibody molecules typically with specificity for a certain cell surface antigen. It could also be, for instance, a hormone having a specific interaction with a cell surface receptor, or a drug having a cell surface receptor. For example, glycolipids could serve to target a polysaccharide receptor. It could also be, for instance, enzymes, lectins, and polysaccharides. Low molecular mass ligands, such as folic acid and derivatives thereof are also useful in the context of the current invention. The targeting molecules can also be polynucleotide, polypeptide, peptidomimetic, carbohydrates including polysaccharides, derivatives thereof or other chemical entities obtained by means of combinatorial chemistry and biology. Targeting molecules can be used to facilitate intracellular transport of the particles of the invention, for instance transport to the nucleus, by using, for example, fusogenic peptides as targeting molecules described by Soukchareun et al., *Bioconjugate Chem.,* 6, 43, (1995) or Arar et al., *Bioconjugate Chem.,* 6, 43 (1995), caryotypic peptides, or other biospecific groups providing site-directed transport into a cell (in particular, exit from endosomic compartments into cytoplasm, or delivery to the nucleus).

Included within the scope of the invention are compositions comprising the polymer networks of the current invention and a suitable targeting molecule. The targeting molecule can be covalently linked to any of the polymer fragments of the polymer networks identified herein, including cationic and nonionic polymer fragments. For instance, the targeting molecule can be linked to the free-terminal or pendant groups of the nonionic fragments of the particles of the invention. Such targeting molecules can be linked to the terminal or pendant —OH end group of the polymer fragments, and the terminal or pendant —$NH_2$ group of the polymers, or the terminal or pendant —COOH end group of the polymers or the like.

It will in some circumstances be desirable to incorporate targeting molecules through ligand-receptor construct, in which (i) the ligand molecule is a chemical entity (e.g., molecule, atom, or ion) capable of specific binding with the receptor molecule, (ii) the receptor molecule is any chemical capable of specific binding to the ligand molecule, (iii) the ligand or receptor molecules or both the ligand and receptor molecules are incorporated in the polymer networks of the current invention or targeting molecules or both polymer networks and targeting molecules, by noncovalent association or covalent conjugation, so that after mixing targeting molecules and polymeric species with ligand and receptor molecules attached to them or adding either free ligand or receptor or both ligand and receptor to the mixture of targeting molecules and polymer networks, the targeting molecule become attached to the polymer networks ad a result of binding between the ligand and receptor. Useful examples of such constructs those using biotin as the ligand and avidin or streptavidin as the receptor. For example, biotin or derivatives thereof can be covalently linked to the polymer networks of the current invention and avidin (or streptavidin) can be covalently linked to the targeting molecule. Alternatively, biotin can be linked to both the polymer networks and targeting molecule and the latter can be linked through avidin, which has four biotin-binding centers. Additionally, more complex constructs comprising biotin and avidin can be used for incorporating targeting molecules in polymer networks of the current invention.

In another embodiment, the invention provides for the polymer networks with biotin molecules or derivatives thereof linked to at least one polyion or nonionic polymer fragment of both polyion and nonionic polymer fragments. Those of ordinary skill in the art will recognize that even when the practice of the invention is confined for example, to biotin-avidin or biotin-streptavidin (or similar) constructs, there are numerous methods available for the design of the ligand-receptor constructs with the desired characteristics pursuant to this invention. Such constructs, for example, can comprise ligands and/or receptors that are polynucleotide, polypeptide, peptidomimetic, carbohydrates including polysaccharides, derivatives thereof or other chemical entities obtained by means of combinatorial chemistry and biology.

The targeting molecules that can be associated with the polymer networks of the current invention can also have a targeting group having affinity for a cellular site and a hydrophobic group. Such targeting molecules can provide for the site-specific delivery and recognition in the body. The targeting molecule will spontaneously associate with the particles and be "anchored" thereto through the hydrophobic group. These targeting adducts will typically comprise about 1% or less of the polymers in a final composition. In the targeting molecule, the hydrophobic group can be, among other things, a lipid group such as a fatty acyl group. Alternately, it can be an ionic or nonionic homopolymer, copolymer, block copolymer, graft copolymer, dendrimer or other natural or synthetic polymer.

The use of the polymer fragments with dual nonionic and anionic functionality in polymer networks of the current invention permits varying of the properties of these systems by changing the lengths and/or chemical structure of these polymer fragments within a very broad range. This design of polymer networks allows for tremendous versatility of properties with simple chemical structures and permits optimization of drug delivery and drug release systems for enhanced performance with a variety of drugs and drug delivery situations. Particularly, the longevity of circulation in the blood can be varied from very long circulating network dispersions to dispersions rapidly accumulating in organs. Biodistribution can be varied to achieve site-specific drug delivery and release, and the rate or release can be varied from seconds to days and weeks, etc. The versatility of these polymer networks permits selecting biological agent compositions that are most efficient and safe (i.e., have best "therapeutic index") for a very broad variety of biological agents. Therefore, this invention also provides for a method of identifying biological agent compositions that can be useful in pharmaceutics and biopharmaceutics, diagnostics and imaging, immunology, veterinary, agriculture, and other areas where the properties of biological agents exhibited during interaction with a living organism or cell can be improved by formulation.

Biological Agents

The polymer networks and compositions of this invention are useful in pharmaceutics and biopharmaceutics, diagnostics and imaging, immunology, veterinary, agriculture, and other areas where the properties of biological agents exhibited during interaction with a living organism or cell can be improved by formulation. The biological agent of this invention is an agent that is useful for diagnostics or imaging or that can act on a cell, organ or organism to create a change in the functioning of the cell, organ or organism, including pharmaceutical drugs, immunoadjuvants, vaccines, genes, herbicides, and the like. Such biological agents are represented by wide variety of agents that are used in diagnostics, therapy, immunization or otherwise are applied to combat human and animal disease. Such agents include nucleic acids, polynucleotides, genes and viruses, antibacterial agents, antiviral agents, antifungal agents, antiparasitic agents, tumoricidal or anti-cancer agents, proteins, toxins, enzymes, hormones, neurotransmitters, glycoproteins, immunoglobulins, immunomodulators, antigens and vaccines, dyes, radiolabels, radio-opaque compounds, fluorescent compounds, polysaccharides, cell receptor binding molecules, anti-inflammatories, anti-glaucomic agents, mydriatic compounds and local anesthetics.

Special classes of biological agents that can be used in this invention include pharmaceutical drugs. Many drugs are rapidly cleared from the body or are degraded by the body's defense mechanisms. These problems, plus toxic side effects, seriously limit drug efficacy by reducing time available to the drug to reach its target and by limiting the amount of drug which can safely be given to the patient. In addition many drugs do not readily penetrate tissues or effectively seek out and concentrate in appropriate cells to maximize their therapeutic effect. The use of the biological agent compositions pursuant to this invention permits significantly improvements to therapeutic drugs by decreasing in their side effects, and increasing their therapeutic action.

Biological agents also include non-steroidal anti-inflammatories such as indomethacin, salicylic acid acetate, ibuprofen, sulindac, piroxicam, and naproxen, antiglaucomic agents such as timolol or pilocarpine, neurotransmitters such as acetylcholine, anesthetics such as dibucaine, neuroleptics such as the phenothiazines (for example compazine, thorazine, promazine, chlorpromazine, acepromazine, amino-promazine, perazine, prochlorperazine, trifluoperazine, and thioproperazine), rauwolfia alkaloids (for example, resperine and deserpine), thioxanthenes (for example chlorprothixene and tiotixene), butyrophenones (for example haloperidol, moperone, trifluoperidol, timiperone, and droperidol), diphenylbutylpiperidines (for example pimozde), and benzamides (for example sulpiride and tiapride); tranquilizers such as glycerol derivatives (for example mephenesin and methocarbamol), propanediols (for example meprobamate), diphenylmethane derivatives (for example orphenadrine, benzotrapine, and hydroxyzine), and benzodiazepines (for example chlordiazepoxide and diazepam); hypnotics (for example zolpdem and butoctamide); beta-blockers (for example propranolol, acebutonol, metoprolol, and pindolol); antidepressants such as dibenzazepines (for example, imipramine), dibenzocycloheptenes (for example, amtiriptyline), and the tetracyclics (for example, mianserine); MAO inhibitors (for example phenelzine, iproniazid, and selegeline); psychostimulants such as phenylehtylamine derivatives (for example amphetamines, dexamphetamines, fenproporex, phentermine, amfeprramone, and pemoline) and dimethylaminoethanols (for example clofenciclan, cyprodenate, aminorex, and mazindol); GABA-mimetics (for example, progabide); alkaloids (for example codergocrine, dihydroergocristine, and vincamine); anti-Parkinsonism agents (for example L-dopamine and selegeline); agents utilized in the treatment of Alzheimer's disease, cholinergics (for example citicoline and physostigmine); vasodilators (for example pentoxifyline); and cerebro active agents (for example pyritinol and meclofenoxate). These agents include also DNA topoisomerase inhibitors (including type I and type II), brain and tumor imaging agents, free radical scavenger drugs, anticoagulants, ionotropic drugs, and neuropeptides such as endorphins.

The biological agent compositions also can be used advantageously with anti-neoplastic agents such as paclitaxel, daunorubicin, doxorubicin, carminomycin, 4'-epiadriamycin, 4-demethoxy-daunomycin, 11-deoxydaunorubicin, 13-deoxy-daunorubicin, adriamycin-14-benzoate, adriamycin-14-actanoate, adriamycin-14-naphthaleneacetate, vinblastine, vincristine, mitomycin C, N-methyl mitomycin C, bleomycin $A_2$, dideazatetrahydrofolic acid, aminopterin, methotrexate, cholchicine and cisplatin, antibacterial agents such as aminoglycosides including gentamicin, antiviral compounds such as rifampicin, 3'-azido-3'-deoxythymidine (AZT), and acylovir; antifungal agents such as azoles including fluconazole, macrolides such as amphotericin B, and candicidin; antiparastic compounds such as antimonials. These biological agents include without limitation vinca alkaloids, such as vincristine and vinblastine, mitomycin-type antibiotics, such as mitomycin C and N-methyl mitomycin, bleomycin-type antibiotics such as bleomycin $A_2$, antifolates such as methotrexate, aminopterin, and dideaza-tetrahydrofolic acid, taxanes, anthracycline antibiotics and others.

The compositions can also utilize a variety of polypeptides such as antibodies, toxins such as diphtheria toxin, peptide hormones, such as colony stimulating factor, and tumor necrosis factors, neuropeptides, growth hormones, erythropoietins, and thyroid hormones, lipoproteins such as p-lipoprotein, proteoglycans such as hyaluronic acid, glycoproteins such as gonadotropin hormone, immunomodulators or cytokines such as interferons or interleukins, and hormone receptors such as the estrogen receptor.

The compositions also can be used with enzyme inhibiting agents such as reverse transcriptase inhibitors, protease inhibitors, angiotensin converting enzymes, 5$\mu$-reductase, and the like. Exemplary agents include peptide and nonpeptide structures such as finasteride, quinapril, ramipril, lisinopril, saquinavir, ritonavir, indinavir, nelfinavir, zidovudine, zalcitabine, allophenylnorstatine, kynostatin, delaviridine, bis-tetrahydrofuran ligands (see, for example Ghosh et al., *J. Med. Chem.* 1996, 39:3278), and didanosine. Such agents can be administered alone or in combination therapy; e.g., a combination therapy utilizing saquinavir, zalcitabine, and didanosine, zalcitabine, and zidovudine. See, for example, Collier et al., *Antiviral Res.* 1996, 29:99.

A wide variety of polynucleotides can be the nucleic acid component of the composition. These includes natural and synthetic DNA or RNA molecules and nucleic acid molecules that have been covalently modified (to incorporate groups including lipophilic groups, photo-induced crosslinking groups, alkylating groups, organometallic groups, intercalating groups, lipophilic groups, biotin, fluorescent and radioactive groups, and groups that modify the phosphate backbone). Such polynucleotides can be, among other things, antisense nucleic acid molecules, gene-encoding single- and double-stranded DNA (usually including an appropriate promoter sequence) such as linear or non-linear plasmids, bacteriophage, viral vectors, DNA vaccines, DNA triplex structures, DNA and RNA mimetics, ribozymes, aptamers, antigen nucleic acids, oligonucleotide α-anomers, ethylphosphotriester analogs, alkylphosphomates, phosphorothionate and phosphorodithionate oligonucleotides, and the like. In fact, the polynucleotides can be any nucleic acid that can beneficially be transported into a cell with greater efficiency, or stabilized from degradative processes, or improved in its biodistribution after administration to an living organism, including humans.

Additional suitable biological agents include viral genomes and viruses (including the lipid and protein coat). This accounts for the possibility of using the invention with a variety of viral vectors in gene delivery (e.g. retroviruses, adenoviruses, herpes-virus, Pox-virus) used as complete viruses of their parts. See, for example, Hodgson, *Biotechnology*, 1995, 13: 222. Other suitable biological agents include oxygen transporters (e.g., porphines, porphirines and their complexes with metal ions), coenzymes and vitamins (e.g., NAD/NADH, vitamins B12, chlorophylls), and the like. Additional suitable biological agents further include the agents used in diagnostics visualization methods, such as magnetic resonance imaging (e.g., gadolinium (III) diethylenetriamine pentaacetic acid), and may be a chelating group (e.g., diethylenetriamine pentaacetic acid, triethylenetriamine pentaacetic acid, ethylenediamine-tetraacetic acid, 1,2-diaminocyclo-hexane-N,N,N',N'-tetraaceticacid, N,N'-di(2-hydroxybenzyl) ethylene diamine), N-(2-hydroxyethyl) ethylene diamine triacetic acid and the like). Such biological agents may further include an alpha-, beta-, or gamma-emitting radionuclide (e.g., galliun 67, indium 111, technetium 99). Suitable biological agents are also iodine containing radiopaque molecules. The biological agent may also be a diagnostic agent, which may include a paramagnetic or superparamagnetic element, or combination of paramagnetic element and radionuclide. The paramagnetic elements include but are not limited to gadolinium (III), dysporsium (III), holmium (III), europium (III) iron (III) or manganese (II).

The invention can be also used to obtain useful fibrinolitic compositions with enzymes such as streptokinase, urokinase, tissue plasminogen activator or other fibrinolitic enzyme that is effective in dissolving blood clots and reestablishing and maintaining blood flow through trombosed coronary or other blood vessels. Also this invention is used to obtain useful compositions for treating burns, circulatory diseases in which there is an acute impairment of circulation, in particular, microcirculation, respiratory distress syndrome, as well as compositions for reducing tissue damage during angioplasty procedures. Further, the compositions identified using this invention include those used to treat myocardial damage, ischemic tissue, tissue damaged by reperfusion injury, stroke, sickle cell anemia and hypothermia. These compositions are particularly useful for treating vascular obstructions caused by abnormal cells which is an often complication during malaria and leukemia, and are suitable as a perfusion medium for transplantation of organs. This invention is also suitable for obtaining compositions of antiinfective compounds, as well as modulators of immune response, and improved adjuvants, antigenes and vaccines.

Adjuvants suitable for use in this invention include adjuvants of mineral, bacterial, plant, synthetic or host product origin. Suitable mineral adjuvants include aluminum compounds such as aluminum particles and aluminum hydroxide. Suitable bacterial adjuvants include but are not limited to muramyl dipeptides, lipid A, *Bordetella pertussis*, Freund's Complete Adjuvant, lipopolysaccharides and its various derivatives, and the like. Suitable adjuvants include without limitation small immunogenes, such as synthetic peptide of malaria, polysaccharides, proteins, bacteria and viruses. Antigenes which can be used in the present invention are compounds which, when introduced into a mammal will result in formation of antibodies. Suitable antigens include natural, recombinant, or synthetic products derived from viruses, bacteria, fungi, parasites and other infectious agents, as well as autoimmune disease, hormones or tumor antigens used in prophylactic or therapeutic vaccines. These antigens include components produced by enzymatic cleavage or can be compounds produced by recombinant DNA technique. Viral antigens include but are not limited to HIV, rotavirus, influenza, foot and mouth disease, herpes simplex, Epstein-Barr virus, Chicken pox, pseudorabies, rabies, hepatitis A, hepatitis B, hepatitis C, measles, distemper, Venezuelan equine encephalomyelitis, Rota virus, polyoma tumor virus, Feline leukemia virus, reovirus, respiratory syncitial virus, Lassa fever virus, canine parvovirus, bovine pappiloma virus, tick borne encephalitis, rinderpest, human rhinovirus species, enterovirus species, Mengo virus, paramixovirus, avian infectious bronchitis virus. Suitable bacterial antigens include but are not limited to *Bordetella pertussis, Brucella abortis, Escherichia coli,* salmonella species, salmonella typhi, streptococci, cholera, shigella, pseudomonas, tuberculosis, leprosy and the like. Also suitable antigens include infections such as Rocky mountain spotted fever and thyphus, parasites such as malaria, schystosomes and trypanosomes, and fungus such as Cryptococcus neoformans. The protein and peptide antigens include subunits of recombinant proteins (such as herpes simplex, Epstein-Barr virus, hepatitis B, pseudorabies, flavivirus, Denge, yellow fever, *Neissera gonorrhoeae,* malaria, trypanosome surface antigen, alphavirus, adenovirus and the like), proteins (such as diphteria toxoid, tetanus toxoid, meningococcal outer membrane protein, streptococcal M protein, hepatitis B, influenza hemagglutinin and the like), synthetic peptides (e.g. malaria, influenza, foot and mouth disease virus, hepatitis B, hepatitis C). Suitable polysaccharide and oligosaccharide antigens originate from pneumococcus, haemphilis influenza, neisseria meningitides, *Pseudomonas aeruginosa, Klebsiella pneumoniae,* pneumococcus.

The present compositions can be used in a variety of treatments including but not limited to improving existing therapies using biological agents, as well as new therapies where formulation of biological agents with polymer networks is beneficial.

For example, the compositions can be used in Gene therapy including gene replacement or excision therapy, and gene addition therapy (B. Huber, Gene therapy for neoplastic diseases; B E Huber and J S Lazo Eds., The New York Academy of Sciences, NY, N.Y., 1994, pp. 6–11). Also, antisense therapy targets genes in the nucleus and/or cytoplasm of the cell, resulting in their inhibition (Stein and Cheng, Science 261:1004, 1993; De Mesmaeker et al., Acc. Chem. Res., 28:366, 1995). Aptamer nucleic acid drugs target both intra-and extracellular proteins, peptides and small molecules. See Ellington and Szostak, *Nature* (London), 346,818, 1990. Antigen nucleic acid compounds can be used to target duplex DNA in the nucleus. See Helene and Tolume, *Biochim, Biophys. Acta* 1049:99 (1990). Catalytic polynucleotides target mRNA in the nucleus and/or cytoplasm (Cech, *Curr. Opp. Struct. Biol.* 2:605,1992).

Examples of genes to be replaced, inhibited and/or added include, but are not limited to, adenosine deaminase, tumor necrosis factor, cell growth factors, Factor IX, interferons (such as $\alpha$-, $\beta$-, and $\gamma$-interferon), interleukins (such interleukin 2, 4, 6 and 12), HLA-B7, HSV-TK, CFTR, HIV-1, $\beta$-2, microglobulin, retroviral genes (such as gag, pol, env, tax, and rex), cytomegalovirus, herpes viral genes (such as herpes simplex virus type I and II genes ICP27/UL54, ICP22/US1, ICP/IE175, protein kinase and exonuclease/ UL13, protein kinase/US3, ribonuclease reductase ICP6/ UL39, immediate early (IE) mRNA IE3/IE175/ICP4, 1E4/ ICP22/US1, IE5/ICP47, IE110, DNA polymerase/UL30, UL13), human multidrug resistance genes (such as mdrl), oncogenes (such as H-c-ras, c-myb, c-myb, bcl-2, bcr/abl), tumor suppressor gene p53, human MHC genes (such as class 1 MHC), immunoglobulins (such as IgG, IgM, IgE, IgA), hemoglobin $\alpha$- and $\beta$-chains, enzymes (such as carbonic anhydrase, triosephoshate isomerase, GTP-cyclhydrdolase I, phenylalanine hydrolase, sarcosine dehydrogenase, glucocerobrosidase, glucose-6-phosphate dehydrogenase), dysotrophin, fibronectin, apoliprotein E, cystic fibrosis transmembrane conductance protein, c-src protein, V(D)J recombination activating protein, immunogenes, peptide and protein antigens ("DNA vaccine") and the like.

Genetic diseases can also be treated by the instant compositions. Such diseases include, but are not limited to, rheumatoid arthritis, psoriasis, Crohn's disease, ulcerative colitis, $\alpha$-thalassemia, $\beta$-thalassemia, carbonic anhydrase II deficiency syndrome, triosephosphate isomerase deficiency syndrome, tetrahydro-biopterindeficient hyperphenylalaniemia, classical phenylketonuria, muscular dystrophy such as Duchenne Muscular Dystrophy, hypersarkosinemia, adenomatous intestinal polyposis, adenosine deaminase deficiency, malignant melanoma, glucose-6-phosphste dehydrogenase deficiency syndrome, arteriosclerosis and hypercholesterolemia, Gaucher's disease, cystic fibrosis, osteopetrosis, increased spontaneous tumors, T and B cell immunodeficiency, high cholesterol, arthritis including chronic rheumatoid arthritis, glaucoma, alcoholism and the like.

The compositions can also be used to treat neoplastic diseases including, but not limited to, breast cancer (e.g., breast, pancreatic, gastric, prostate, colorectal, lung, ovarian), lymphomas (such as Hodgkin and non-Hodgkin lymphoma), melanoma and malignant melanoma, advanced cancer hemophilia B, renal cell carcinoma, gliblastoma, astrocytoma, gliomas, AML and CML and the like.

Additionally, the compositions can be used to treat (i) cardiovascular diseases including but not limited to stroke, cardiomyopathy associated with Duchenne Muscular Dystrophy, myocardial ischemia, restenosis and the like, (ii) infectious diseases such as Hepatitis, HIV infections and AIDS, Herpes, CMV and associated diseases such as CMV renitis, (iii) transplantation related disorders such as renal transplant rejection and the like, and (iv) are useful in vaccine therapies and immunization, including but not limited to melanoma vaccines, HIV vaccines, malaria, tuberculosis, and the like.

Target Cells

Cell targets can be ex vivo or in vivo, and includes, but is not limited to, T and B lymphocytes, primary CML, tumor infiltrating lymphocytes, tumor cells, leukemic cells (such as HL-60, ML-3, KG-1 and the like), skin fibroblasts, myoblasts, cells of central nervous system including primary neurons, liver cells, carcinoma (such as Bladder carcinoma T24, human colorectal carcinoma Caco-2), melanoma, CD34[+] lymphocytes, NK cells, macrophages, hemotopoetic cells, neuroblastoma (such as LAN-5 and the like), gliomas, lymphomas (such as Burkitt lymphomas ST486), JD38), T-cell hybridomas, muscle cells such as primary smooth muscle, dermal cells, and the like.

Surfactant-Containing Compositions

The invention also provides compositions having a polymer network and at least one surfactant. Surfactants are useful for improving the solubility of biological agents, changing the properties (e.g. particle size, aggregation stability, bioavailability, cell transport) of the polymer networks and compositions of the current invention, improving shelf life and the like. It is believed that surfactants can alter the conformation of the polymer fragments by interacting with them. Such alteration occurs during interaction of the polyanion fragments of the polymer networks with cationic surfactants resulting in the collapse of these fragments and condensation of the nanogel particles. For example, the polyoxyethylene-poly(acrylic acid) networks interact with cetylpyridinium bromide. Another example is the interaction of nonionic and ionic amphiphilic surfactants with nonionic fragments, e.g. polyoxyethylene-polyoxypropylene fragments. Also, anionic surfactants can interact with nonionic fragments, e.g. alkylsufates interacting with polyoxyethylene. Finally, surfactants can form hydrogen bonds with the nanogel chains. For example, the hydrogen binding of nonionic polyoxyethylene-polyoxypropylene surfactants with poly(acrylic acid) at pH 5.0.

The addition of surfactant to the polymer network containing compositions can be used to vary in a controllable manner the porosity and stability of the network, adjust the size of the nanogel particles, and modify variety of properties of the polymer networks and the biological agent compositions thereof that are relevant to the effects on a living organism or cell.

Surfactants as defined herein are most generally surface active agents that are adsorbed at interface (see, for example, Martin, *Physical Pharmacy,* $4^{th}$ edn., p. 370 et seq., Lea & Febiger, Philadelphia, London, 1993). These surface active agents in particular decrease the surface tension at the air-water interface in aqueous solutions th (see, for example, Martin, Physical Pharmacy, 4 edn., p. 370 et seq., Lea & Febiger, Philadelphia, London, 1993) and include without limitation micelle forming amphiphiles, soaps, lipids, surface active drugs and other surface active biological agents, and the th like (see, for example, Martin, *Physical Pharmacy,* $4^{th}$ edn., Lea & Febiger, Philadelphia, London, 1993; Marcel Dekker, New York, Basel, 1979; Atwood and Florence, *J. Pharm. Pharmacol.* 1971, 23:242S; Atwood and Florence, *J. Pharm. Sci.* 1974, 63:988; Florence and Attwood, *Physicochemical Principles of Pharmacy,* $2^{nd}$ edn., p.180 et seq., Chapman and Hall, New York, 1988; Hunter, *Introduction to Modern Colloid Science,* p. 12 et seq., Oxford University Press, Oxford, 1993). The surfactant can be (i) cationic (including those used in various transfection cocktails), (ii) nonionic (e.g., Pluronic or Tetronic), (iii) zwitterionic (including betains and phospholipids), or (iv) anionic (e,g., salts of fatty acids).

Cationic surfactants suitable for use in present biological agent compositions include primary amines (e.g., hexylamine, heptylamine, octylamine, decylamine, undecylamine, dodecylamine, pentadecyl amine, hexadecyl amine, oleylamine, stearylamine, diaminopropane, diaminobutane, diaminopentane, diaminohexane, diaminoheptane, diaminooctane, diaminononane, diaminodecane, diaminododecane), secondary amines (e.g., N,N-distearylamine), tertiary amines (e.g., N,N',N'-polyoxyethylene(10)-N-tallow-1,3-diaminopropane), quaternary amine salts (e.g., dodecyltrimethylammonium bromide, hexadecyltrimethylammonium bromide, alkyltrimethylammonium bromide, tetradecyltrimethylammonium bromide, benzalkonium chloride, cetyidimethylethylammonium bromide, dimethyldioctadecyl ammonium bromide, methylbenzethonium chloride, decamethonium chloride, methyl mixed trialkyl ammonium chloride, methyl trioctylammonium chloride), 1,2-diacyl-3-(trimethylammonio) propane (acyl group=dimyristoyl, dipalmitoyl, distearoyl, dioleoyl), 1,2-diacyl-3-(dimethylammonio)propane (acyl group=dimyristoyl, dipalmitoyl, distearoyl, dioleoyl), 1,2-dioleoyl-3-(4'-trimethylammonio) butanoyl-sn-glycerol, 1,2-dioleoyl-3-succinyl-sn-glycerol choline ester, cholesteryl (4'-trimethylammonio) butanoate), N-alkyl pyridinium and quinaldinium salts (e.g., cetylpyridinium halide, N-alkylpiperidinium salts, dialkyldimetylammonium salts, dicationic bolaform electrolytes ($C_{12}Me_6$; $C_{12}Bu_6$), dialkylglycetylphosphorylcholine, lysolecithin), cholesterol hemisuccinate choline ester, lipopolyamines (e.g., dioctadecylamidoglycylspermine (DOGS), dipalmitoyl phosphatidylethanolamidospermine (DPPES), N'-octadecylsperminecarboxamide hydroxytrifluoroacetate, N',N"-dioctadecylsperminecarboxamide hydroxytrifluoroacetate, N'-nonafluoropentadecylosperminecarboxamide hydroxytrifluoroacetate, N',N"-dioctyl(sperminecarbonyl) glycinamide hydroxytrifluoroacetate, N'-(heptadecafluorodecyl)-N'-(nonafluoropentadecyl)-sperminecarbonyl)glycinamede hydroxytrifluoroacetate, N'-[3,6,9-trioxa-7-(2'-oxaeicos-11'-enyl)heptaeicos-18-enyl]-sperminecarboxamide hydroxy-trifluoroacetate, N'-(1,2-dioleoyl-sn-glycero-3-phosphoethanoyl)spermine carboxamide hydroxytrifluoroacetate) (see, for example, Behr et. al., *Proc. Natl. Acad. Sci.* 1989, 86:6982; Remy et al., *Bioconjugate Chem.* 1994, 5:647), 2,3-dioleyloxy-N-[2 (spermine-carboxamido)ethyl]-N,N-dimethyl-1-propanaminiumtrifluoroacetate (DOSPA) (see, for example, Ciccarone et al., *Focus* 1993, 15:80), N,$N^{I}$,$N^{II}$,$N^{III}$-tetramethyl-N,$N^{I}$,$N^{II}$,$N^{III}$-tetrapalmitylspermine (TM-TPS) (Lukow et al., *J. Virol.,* 1993, 67:4566), N-[1-(2,3-dioleyloxy)propyl]-N,N,N-trimethylamonium chloride (DOTMA) (see, for example, Felgner, et al., *Proc. Natl. Acad. Sci.* USA 1987, 84:7413; Ciccarone et al., *Focus* 1993, 15:80), dimethyl dioctadecylammonium bromide (DDAB) (see, for example, Whitt et al., *Focus* 1991, 13:8), 1,2-dioleoyl-3-dimethyl-hydroxyethyl ammonium bromide (DORI) (see, for example, Felgner et al., *J. Biol. Chem.* 1994, 269:2550), 1,2-dioleyloxypropyl-3-dimethyl-hydroxyethyl ammonium bromide (DORIE) (see, for example, Felgner et al., *J. Biol. Chem.* 1994, 269:2550), 1,2-dioleyloxypropyl-3-dimethyl-hydroxypropyl ammonium bromide (DORIE-HP) (see, for example, Felgner et al., *J. Biol. Chem.* 1994, 269:2550), 1,2-dioleyloxypropyl-3-dimethyl-hydroxybutyl ammonium bromide (DORIE-HB) (see, for example, Feigner et al., *J. Biol. Chem.* 1994, 269:2550), 1,2-dioleyloxypropyl-3-dimethyl-hydroxypentyl ammonium bromide (DORIE-HPe) (see, for example, Felgner et al., *J. Biol. Chem.* 1994, 269:2550), 1,2-dimyristyloxypropyl-3-dimethyl-hydroxyethyl ammonium bromide (DMRIE) (see, for example, Felgner et al., *J. Biol. Chem.* 1994, 269:2550), 1,2-dipalmitoyloxypropyl-3-dimethyl-hydroxyethyl ammonium bromide (DPRIE) (see, for example, Felgner et al., *J. Biol. Chem.* 1994, 269:2550), 1,2-distearoyloxypropyl-3-dimethyl-hydroxyethyl ammonium bromide (DSRIE) (see, for example, Felgner et al., *J. Biol. Chem.* 1994, 269:2550), N,N-dimethyl-N-[2-(2-methyl-4-(1,1,3,3-tetramethylbutyl)-phenoxy]ethoxy) ethyl]-benzenemethanaminium chloride (DEBDA), N-[1-(2,3-dioleyloxy)propyl]-N,N,N,-trimethylammonium methylsulfate (DOTAB), lipopoly-L(or D)-lysine (see, for example, Zhou, et al., Biochim. Biophys. Acta 1991, 1065:8), poly(L (or D)-lysine conjugated to N-glutarylphosphatidylethanolamine lysine (see, for example, Zhou, et al., Biochim. Biophys. Acta 1991, 1065:8), didodecyl glutamate ester with pendant amino group ($C_{12}GluPhC_nN^+$) (see, for example, Behr, *Bioconjugate Chem.,* 1994, 5:382), ditetradecyl glutamate ester with pendant amino group ($C_{14}GluC_nN^+$) (see, foe example, Behr, *Bioconjugate Chem.* 1994, 5:382), 9-(N',N"-dioctadecylglycinamido)acridine (see, for example, Remy et al., *Bioconjugate Chem.* 1994, 5:647), ethyl 4-[[N-[3-bis (octadecylcarbamoyl)-2-oxapropylcarbonyl]glycinamido] pyrrole-2-carboxamido]-4-pyrrole-2-carboxylate (see, for example, Remy et al., *Bioconjugate Chem.* 1994, 5:647), N',N'-dioctadecylornithylglycinamide hydroptrifluoroacetate (see, for example, Remy et al., *Bioconjugate Chem.* 1994, 5:647), cationic derivatives of cholesterol (e.g., cholesteryl-3β-oxysuccinamidoethylenetrimethylammonium salt, cholesteryl-3β-oxy-succinamidoethylenedimethylamine, cholesteryl-3β-carboxyamidoethylenetrimethyl-ammonium salt, cholesteryl-3β-carboxyamidoethylenedimethylamine, 3β[N-(N',N'-dimethylaminoetane-carbomoyl] cholesterol) (see, for example, Singhal and Huang, In *Gene Therapeutics,* Wolff, Ed., p. 118 et seq., Birkhauser, Boston, 1993), pH-sensitive cationic lipids (e.g., 4-(2,3-bis-palmitoyloxy-propyl)-1-methyl-1H-imidazole, 4-(2,3-bis-oleoyloxy-propyl)-1-methyl-1H-imidazole, cholesterol-(3-imidazol-1-yl propyl) carbamate, 2,3-bis-palmitoyl-propyl-pyridin-4-yl-amine) and the like (see, for example, Budker, et al. *Nature Biotechnology* 1996, 14:760).

Especially useful in the context of gene delivery and other applications are the compositions with the mixtures of cationic surfactant and nonionic surfactants including dioloeoyl phosphatidylethanolamine (DOPE), dioleoyl phosphatidylcholine (DOPC) (see, for example, Feigner, et al., *Proc. Natl. Acad. Sci. USA* 1987; Singhal and Huang, In *Gene Therapeutics,* Wolff, Ed., p. 118 et seq., Birkhauser, Boston, 1993). This includes, in particular, commercially available cationic lipid compositions including LipofectAMINE™, Lipofectine®, DMRIE-C, CellFICTIN™, LipofectACE™, Transfectam reagents (see, for example, Ciccarone et al., *Focus* 1993, 15:80; Lukow et al., *J. Virol.* 1993, 67:4566; Behr, *Bioconjugate Chem.* 1994, 5:382; Singhal and Huang, In *Gene Therapeutics,* Wolff, Ed., p. 118 et seq., Birkhauser, Boston, 1993; GIBCO-BRL Co.; Promega Co., Sigma Co) and other cationic lipid compositions used for transfection of cells (see, for example, Feigner et al., *J. Biol. Chem.* 1994, 269:2550; Budker, et al. *Nature Biotechnology* 1996,14:760).

Suitable anionic surfactants for use in the present biological agent compositions include alkyl sulfates, alkyl sulfonates, fatty acid soap including salts of saturated and unsaturated fatty acids and derivatives (e.g., arachidonic acid, 5,6-dehydroarachidonic acid, 20-hydroxyarachidonic acid, 20-trifluoro arachidonic acid, docosahexaenoic acid, docosapentaenoic acid, docosatrienoic acid, eicosadienoic acid, 7,7-dimethyl-5,8-eicosadienoic acid, 7,7-dimethyl-5,8-eicosadienoic acid, 8,11-eicosadiynoic acid, eicosapentaenoic acid, eicosatetraynoic acid, eicosatrienoic acid, eicosatriynoic acid, eladic acid, isolinoleic acid, linoelaidic acid, linoleic acid, linolenic acid, dihomo-γ-linolenic acid, γ-linolenic acid, 17-octadecynoic acid, oleic acid, phytanic acid, stearidonic acid, 2-octenoic acid, octanoic acid, nonanoic acid, decanoic acid, undecanoic acid, undecelenic acid, lauric acid, myristoleic acid, myristic acid, palmitic acid, palmitoleic acid, heptadecanoic acid, stearic acid, nonanedecanoic acid, heneicosanoic acid, docasanoic acid, tricosanoic acid, tetracosanoic acid, cis-15-tetracosenoic acid, hexacosanoic acid, heptacosanoic acid, octacosanoic acid, triocantanoic acid), salts of hydroxy-, hydroperoxy-, polyhydroxy-, epoxy-fatty acids (see, for example, Ingram and Brash, *Lipids* 1988, 23:340; Honn et al., *Prostaglandins* 1992, 44:413; Yamamoto, *Free Radic. Biol. Med.* 1991, 10:149; Fitzpatrick and Murphy, *Pharmacol. Rev.* 1989, 40:229; Muller et al., *Prostaglandins* 1989, 38:635; Falgueyret et al., *FEBS Lett* 1990, 262:197; Cayman Chemical Co., 1994 Catalog, pp. 78–108), salts of carboxylic acids (e.g., valeric acid, trans-2,4-pentadienoic acid, hexanoic acid, trans-2-hexenoic acid, trans-3-hexenoic acid, 2,6-heptadienoic acid, 6-heptenoic acid, heptanoic acid, pimelic acid, suberic acid, sebacicic acid, azelaic acid, undecanedioic acid, decanedicarboxylic acid, undecanedicarboxylic acid, dodecanedicarboxylic acid, hexadecanedioic acid, docasenedioic acid, tetracosanedioic acid, agaricic acid, aleuritic acid, azafrin, bendazac, benfurodil hemisuccinate, benzylpenicillinic acid, p-(benzylsulfonamido)benzoic acid, biliverdine, bongkrekic acid, bumadizon, caffeic acid, calcium 2-ethylbutanoate, capobenic acid, carprofen, cefodizime, cefmenoxime, cefixime, cefazedone, cefatrizine, cefamandole, cefoperazone, ceforanide, cefotaxime, cefotetan, cefonicid, cefotiam, cefoxitin, cephamycins, cetiridine, cetraric acid, cetraxate, chaulmoorgic acid, chlorambucil, indomethacin, protoporphyrin IX, protizinic acid), prostanoic acid and its derivatives (e.g., prostaglandins) (see, for example, Nelson et al., *C&EN* 1982, 30–44; Frolich, *Prostaglandins,* 1984, 27:349; Cayman Chemical Co., 1994 Catalog, pp. 26–61), leukotrienes and lipoxines (see for example, Samuelsson et al., *Science* 1987, 237:1171; Cayman Chemical Co., 1994 Catalog, pp. 64–75), alkyl phosphates, O-phosphates (e.g., benfotiamine), alkyl phosphonates, natural and synthetic lipids (e.g., dimethylallyl pyrophosphate ammonium salt, S-farnesylthioacetic acid, farnesyl pyrophosphate, 2-hydroxymyristic acid, 2-fluorpalmitic acid, inositoltrphosphates, geranyl pyrophosphate, geranygeranyl pyrophosphate, α-hydroxyfarnesyl phosphonic acid, isopentyl pyrophoshate, phosphatidylserines, cardiolipines, phosphatidic acid and derivatives, lysophosphatidic acids, sphingolipids and like), synthetic analogs of lipids such as sodium-dialkyl sulfosuccinate (e.g., Aerosol OT®), n-alkyl ethoxylated sulfates, n-alkyl monothiocarbonates, alkyl- and arylsulfates (asaprol, azosulfamide, p-(benzylsulfonamideo) benzoic acid, cefonicid, CHAPS), mono- and dialkyl dithiophosphates, N-alkanoyl-N-methylglucamine, perfluoroalcanoate, cholate and desoxycholate salts of bile acids, 4-chloroindoleacetic acid, cucurbic acid, jasmonic acid, 7-epi jasmonic acid, 12-oxo phytodienoic acid, traumatic acid, tuberonic acid, abscisic acid, acitertin, and the like. Preferred cationic and anionic surfactants also include fluorocarbon and mixed fluorocarbon-hydrocarbon surfactants. See for example, Mukerjee, P. *Coll. Surfaces A: Physicochem. Engin. Asp.* 1994, 84: 1; Guo et al. *J. Phys. Chem.,* 1991, 95: 1829; Guo et al. *J. Phys. Chem.,* 1992, 96: 10068. Suitable surfactants includes salts of perfluorocarboxylic acids (e.g., pentafluoropropionic acid, heptafluorobutyric acid, nonanfluoropentanoic acid, tridecafluoroheptanoic acid, pentadecafluorooctanoic acid, heptadecafluorononanoic acid, nonadecafluorodecanoic acid, perfluorododecanoic acid, perfluorotetradecanoic acid, hexafluoroglutaric acid, perfluoroadipic acid, perfluorosuberic acid, perfluorosebacicic acid), double tail hybrid surfactants $(C_mF_{2m+1})(C_nH_{2n+1})CH—OSO_3Na$ (see, for example, Guo et al. *J. Phys. Chem.* 1992, 96: 6738, Guo et al. *J. Phys. Chem.* 1992, 96: 10068; Guo et al. *J. Phys. Chem.* 1992, 96: 10068), fluoroaliphatic phosphonates, fluoroaliphatic sulphates, and the like).

The biological agent compositions may additionally contain nonionic or zwitterionic surfactants including but not limited to phospholipids (e.g., phosphatidylethanolamines, phosphatidylglycerols, phosphatidylinositols, diacyl phosphatidyl-cholines, di-O-alkyl phosphatidylcholines, platelet-activating factors, PAF agonists and PAF antagonists, lysophosphatidylcholines, lysophosphatidylethanolamines, lysophosphatidylglycerols, lysophosphatidylinositols, lyso-platelet-activating factors and analogs, and the like), saturated and unsaturated fatty acid derivatives (e.g., ethyl esters, propyl esters, cholesteryl esters, coenzyme A esters, nitrophenyl esters, naphtyl esters, monoglycerids, diglycerids, and triglycerides, fatty alcohols, fatty alcohol acetates, and the like), lipopolysaccharides, glyco- and shpingolipids (e.g. ceramides, cerebrosides, galactosyldiglycerids, gangliosides, lactocerebrosides, lysosulfatides, psychosines, shpingomyelins, sphingosines, sulfatides), chromophoric lipids (neutral lipids, phospholipids, cerebrosides, sphingomyelins), cholesterol and cholesterol derivatives, n-alkylphenyl polyoxyethylene ether, n-alkyl polyoxyethylene ethers (e.g., Triton™), sorbitan esters (e.g., Span™), polyglycol ether surfactants (Tergitol™), polyoxy-ethylenesorbitan (e.g., Tween™), polysorbates, polyoxyethylated glycol monoethers (e.g., Brij™, polyoxylethylene 9 lauryl ether, polyoxylethylene 10 ether, polyoxylethylene 10 tridecyl ether), lubrol, copolymers of ethylene oxide and propylene oxide (e.g., Pluronic™, Pluronic R™, Teronic™, Pluradot™), alkyl aryl polyether alcohol (Tyloxapol™), perfluoroalkyl polyoxylated amides, N,N-bis[3-D-gluconamido-propyl]cholamide, decanoyl-N-methylglucamide, n-decyl α-D-glucopyranozide, n-decyl β-D-glucopyranozide, n-decyl β-D-maltopyranozide, n-dodecyl β-D-glucopyranozide, n-undecyl β-D-glucopyranozide, n-heptyl β-D-glucopyranozide, n-heptyl β-D-thioglucopyranozide, n-hexyl β-D-glucopyranozide, n-nonanoyl β-D-glucopyranozide 1-monooleyl-rac-glycerol, nonanoyl-N-methylglucamide, n-dodecyl α-D-maltoside, n-dodecyl β-D-maltoside, N,N-bis[3-gluconamidepropyl] deoxycholamide, diethylene glycol monopentyl ether, digitonin, heptanoyl-N-methylglucamide, heptanoyl-N-methylglucamide, octanoyl-N-methylglucamide, n-octyl β-D-glucopyranozide, n-octyl α-D-glucopyranozide, n-octyl β-D-thiogalactopyranozide, n-octyl β-D-thioglucopyranozide, betaine ($R_1R_2R_3N^+R'CO_2^-$, where $R_1R_2R_3R'$ hydrocarbon chains), sulfobetaine ($R_1R_2R_3N+R'$ $SO_3^-$), phoshoplipids (e.g. dialkyl phosphatidylcholine), 3-[(3-cholamidopropyl)-dimethylammonio]-2-hydroxy-1-propanesulfonate, 3-[(3-cholamidopropyl)-dimethylammonio]-1-propanesulfonate, N-decyl-N,N-dimethyl-3-ammonio-1-propanesulfonate, N-dodecyl-N,N-dimethyl-3-ammonio-1-propanesulfonate, N-hexadecyl-N,N-dimethyl-3-ammonio-1-propanesulfonate, N-octadecyl-N,N-dimethyl-3-ammonio-1-propane-sulfonate, N-octyl-N,N-dimethyl-3-ammonio-1-propanesulfonate, N-tetradecyl-N,N-dimethyl-3-ammonio-1-propanesulfonate, and dialkyl phosphatitidyl-ethanolamine.

Polymer Blends

The polymer networks and the compositions thereof can be blended with various natural and synthetic polymers to improve stability, bioavailability, incorporation of biological agents, shelf-life and other properties that are relevant to the effects on the living organism and cell. Such natural and synthetic polymers can be cationic, anionic or nonionic include homopolymers, copolymers, block copolymers, graft copolymers or dendrimers of ethylene oxide, propylene oxide, butylene oxide, carbohydrates, acrylamide, acrylic esters, methacrylamide, N-(2-hydroxypropyl)-methacrylamide, vinyl alcohol, vinyl pyrrolidone, vinyltriazole, vinylpyridine and its N-oxide, ortho esters, amino acids, nucleic acids, acrylic acid, methacrylic acid, heparin, phosphate, malic acid, lactic acid, carboxylated dextran, alkylene imine, ethyleneimine, amidoamines, vinylpyridinium salts, ionenes methacrylates, dimethylaminoethyl methacrylate, trimethylamonioethyl methacrylate and the like. Polymer blends useful in this invention are complexes formed by anionic nanogels and cationic polymers, such as polyethyleneimine, polyallylamine, polyetheramine, polyvinylpyridine, polyamine acids, polylysine and the like.

The polymer networks and compositions thereof can be administered orally, topically, rectally, vaginally, by pulmonary route by use of an aerosol, or parenterally, i.e., intramuscularly, subcutaneously, intraperitoneally or intravenously. The polymer networks and compositions thereof can be administered alone, or can be combined with a pharmaceutically-acceptable carrier or excipient according to standard pharmaceutical practice. For oral administration, the polymer networks and compositions thereof can be used in the form of tablets, capsules, lozenges, troches, powders, syrups, elixirs, aqueous solutions and suspensions, and the like. For tablets, suitable carriers include lactose, sodium citrate and salts of phosphoric acid. Various disintegrates such as starch, and lubricating agents such as magnesium stearate, sodium lauryl sulfate and talc, are commonly used in tablets. For oral administration in capsule form, useful diluents include lactose and high molecular weight polyethylene glycols. When aqueous suspensions are required for oral use, the polymer networks and compositions thereof can be combined with emulsifying and suspending agents. If desired, certain sweetening and/or flavoring agents can also be added. For parenteral administration, sterile solutions of the polymer networks and compositions thereof are usually prepared, and the pH of the solutions suitably adjusted and buffered. For intravenous use, the total concentration of solutes is controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. For pulmonary administration, diluents and/or carriers can be selected to allow the formation of an aerosol.

The following examples will serve to further typify the nature of the invention but should not be construed as a limitation on the scope thereof, which is defined solely by the appended claims.

EXAMPLE A

Synthesis of Bis-carbonyldiimidazole-activated Poly (Ethylene Glycol)

Bis-carbonyldiimidazole-activated poly(ethylene glycol) was synthesized by treating poly(ethylene glycol), M.W. 4,600, (Aldrich) with 10-fold excess of 1,1'-carbonyidiimidazole. A solution of 1.8 g (10 mmol) of 1,1'-carbonyldiimidazole in 10 ml of anhydrous acetonitrile was added in small portions to 8.0 g (1 mmol) of poly (ethylene glycol) in 20 ml of anhydrous acetonitrile with constant stirring. Reaction was carried out in for 17 hrs at 40° C. Then the reaction mixture was diluted by water and dialyzed against water for 24 hrs. Products were obtained after lyophilization as white solids with near quantitative yields.

EXAMPLE 1

Synthesis of Nanogel I Networks from Polyacrylic Acid and Poly(Ethylene Glycol)

A solution of 0.9 g of the sodium salt of polyacrylic acid (PM), M.w. 30,000, was dialyzed against 0.01 N HCl and then converted into diisopropylethylammonium (DIPEA) salt by titration with DIPEA up to pH 7.5. 0.9 g of PEG-(amino)2, M.w. 3,400 (Shearwater Polymers), was added to the previous solution to obtain the PEG/PAA molar ratio equal to 10 and, finally, total mixture was lyophilized. Dry material was dissolved in 4 ml of water to obtain 30% w/v solution.

A solution of 0.4 g (2.1 mmol) of water-soluble activation agent, 1-ethyl-3(3-dimethylaminopropyl)carbodiimide (EDC), in 1 ml of water was mixed with the previously prepared polymer solution. Final reaction mixture was immediately added to 200 ml of vigorously stirring 20 mM solution of dioctyl sulfosuccinate (AOT) in dichloroethane. White emulsion was additionally dispersed by sonication for 20 min at 25° C. in ultrasonic cleaner water bath at 80 W. Gel formation could be observed on the walls of the reaction flask. The mixture was diluted by water (200 ml) and dichloroethane was then removed by rotor evaporation in vacuo at 40° C. Transparent suspension was diluted with ethanol up to 20% v/v and left for 17 hrs at 25° C. for cross-linking reaction to complete. Large debris was separated by centrifugation for 20 min at 2,000 g. Supernatant was dialyzed twice against 20 mM phosphate buffer, pH 7.4, for 4 hrs and water for 18 hrs in semi-permeable membrane bag, cutoff 3,500, and concentrated in vacuo. Nanogel I was obtained after lyophilization as white solid with yield of 65%.

Effective diameter of anionic nanogel I particles in aqueous dispersion was 156 nm.

EXAMPLE 2

Synthesis of Nanogel II Networks from Polyacrylic Acid and Poly(Ethylene Glycol)

Following the procedure of Example 1 but substituting 0.9 g of bis-ethylenediamino-poly(ethylene glycol), M.w. 8,000, for 0.9 g of PEG-(amino)2, M.w. 3,400, nanogel II was obtained. Bis-ethylenediamino-poly(ethylene glycol) was synthesized from the corresponding bis-carbonyidiimidazole-activated poly(ethylene glycol) (see EXAMPLE #A) by reaction with the excess of ethylenediamine. 2 g of bis-ethylenediamino-poly(ethylene glycol), M.w. 8,000, was dissolved in 20 ml of 50% ethanol, ethylenediamine (0.3 g) was added and the reaction mixture was stirred for 18 hrs at 25° C. The excess of ethylenediamine was removed by dialysis in semi-permeable membrane bag, cutoff 3,500, against water for 24 hrs at 25° C. Product was obtained after lyophilization with practically quantitative yield.

Effective diameter of anionic nanogel II particles in aqueous dispersion was 283 nm.

EXAMPLE 3

Synthesis of Nanogel Networks from Polyacrylic Acid and Pluronic P123

A. Bis-carbonyldiimidazole-activated Pluronic P123 from Pluronic P123 (BASF Co.) by following the procedure of Example A but substituting 8 g of poly(ethylene glycol), MW 4,600 for 5.8 g (1 mmol) of Pluronic F38 for the same amount of mono-4,4'-dimethoxytrityl-derivative of Pluronic F123. Bis-ethylenediamino-Pluronic P123 was obtained from the activated Pluronic P123 as described in Example #2 with near quantitative yields. Amino group amount in the product was determined by fluorescamine method as described by Weigele et al. (*J. Amer. Chem. Soc.,* 1972, 94: 5927) and corresponded to 88–93% of theoretical substitution rate.

B. 45 ml of 2% solution of polyacrylic acid, M.w. 30,000, in the form of DIPEA-salt obtained as described in Part A of Example 1 and 0.4 g (2 mmol) of EDC were incubated for 1 hrs at 25° C. The activated polymer solution was added to the intensively stirred 1% solution of bis-ethylenediamino-Pluronic P123 in 100 ml of water. After 2 days incubation at room temperature under constant stirring the mixture was charged to semi-permeable membrane bag, cutoff 6,000–7,000 and dialyzed twice against 20% ethanol and water for 17 hrs at 25° C. Nanogel III suspension was concentrated in vacuo and then lyophilized giving white solid product with yield of 85%.

Effective diameter of anionic nanogel III particles in aqueous dispersion was 193 nm.

EXAMPLE 4

Fractionation of Nanogel Particles and Size Determination

Lyophilized nanogel particles obtained in Examples 1–3 were each dissolved in the solution containing 0.2M sodium chloride and 20% ethanol at concentration ca. 0.25 g of crude product/ml. 5 ml of each Nanogel solution was applied on the column (2.5×85 cm) with Sepharose CL-2B and eluted by the same solution at flow rate 1 ml/min. A refractive index detector was used to visualize the eluted products. High-molecular weight products were collected and dialyzed against water in semi-permeable membrane bag, cutoff 3,500 for 17 hrs at 25° C. Desalted products were concentrated in vacuo and lyophilized. The dimensions of the nanogel particles were determined after resuspension using "ZetaPlus" Zeta Potential Analyzer (Brookhaven Instrument Co.) with 15 mV solid state laser operated at a laser wavelength of 635 nm and equipped with Multi Angle Option.

In the nanogel I preparation, the first half of the main peak (7.5 ml/tube, fractions 31–41) contained 1.2 g, the second half (fractions 42–49) contained 0.55 g of polymeric products. Chemical analysis of the high molecular weight part of the peak resulted in the following nitrogen content: theor. 0.38%, found 0.33%. Molecular ratio of poly(ethylene glycol) to polyacrylic acid determined from the nitrogen content data equaled 9. Particle size was 156 nm.

In the nanogel II preparation, the first half of the main peak (7.5 ml/tube, fractions 27–38) contained 1.05 g, the second half (fractions 39–48) contained 0.45 g of polymeric products. Chemical analysis of the high molecular weight part of the peak resulted in the following nitrogen content: theor. 0.17%, found 0.16%. Molecular ratio of poly(ethylene glycol) to polyacrylic acid determined from the nitrogen content data equaled 5. Particle size was 283 nm.

In the nanogel III preparation, the main peak (7.5 ml/tube, fractions 31–41) contained 1.6 g of polymeric products. Chemical analysis of the peak resulted in the following nitrogen content: theor. 0.22%, found 0.23%. Molecular ratio of Pluronic P123 to polyacrylic acid determined from the nitrogen content data equaled 6. Particle size was 193 nm.

Nanogel samples were characterized by size distribution in the range 0.29–0.33.

EXAMPLE 5

Preparation of NanoGel Compositions with Cetylpyridinium Bromide

A suspension of Nanogel 1 was prepared in phosphate buffer pH 7.4 by sonication of 1 mg/ml Nanogel 1 sample for 30 min at 25° C. 50 mM solution of cetylpyridinium bromide was added dropwise to the suspension of Nanogel 1. The particle size at various charge ratios: Z=[surfactant]/[COOH] was measured using "ZetaPlus" Zeta Potential Analyzer (Brookhaven Instrument Co.) with 15 mV solid state laser operated at a laser wavelength of 635 nm. Before each measurement the Nanogel 1 suspension was incubated for 10 min. at 25° C. The results at different Z were as follows:

| $Z_{-/+}$ | 0 | 0.3 | 0.6 | 0.9 | 1 | 1[a] |
|---|---|---|---|---|---|---|
| Effective diameter, nm | 150 | 130 | 100 | 60 | 80 | 80 |

[a]After 48 hour incubation.

At the charge neutralization point (Z=1) a clear suspension was obtained with no sign of aggregation and with effective diameter ca. 8o nm, which is 2 times less than initial non-loaded Nanogel 1 particles. The particle size at Z 1 did not change after 48 hr. incubation.

EXAMPLE 6

Preparation and Characterization of Nanogel Compositions with Doxorubicin 10 mg/ml suspension of nanogel III described in Example 3 was obtained by resuspension of lyophilized nanogel III sample in phosphate buffered saline, pH 7.4 (PBS), sonication for 30 min at 25° C. and filtration through 0.45 $\mu$m disposable filter. A positively charged drug doxorubicin, containing hydrophobic anthracyclin group is used in this example to prepare the composition. Doxorubicin solutions were prepared at 1 mg/ml concentration in PBS and filtered through 0.22 $\mu$m disposable filter. The calculated volume of the drug solution was added dropwise into the stirred suspension of nanogel III to obtain 10 uM stock solution and final mixture was incubated for 1 hr at 37° C. The particle size was measured using "ZetaPlus" Zeta Potential Analyzer (Brookhaven Instrument Co.). The nanogel particles are formed with effective diameter ca. 80 to 160 nm. The nanogel loading capacity with respect to doxorubicin was ca. 0.3 mg of doxorubicin per 1 mg of nanogel.

EXAMPLE 7

Preparation and Characterization of Nanogel Compositions with Insulin

Insulin solution (1 mg/ml) was prepared in 50 mM sodium bicarbonate, pH 8.5, and filtered through 0.22 $\mu$m disposable filter. The calculated volume of this solution was added dropwise to the nanogel III suspension prepared as described in Example 6. The mixture was incubated for 5 hrs at 4° C. and the particle size was measured using "ZetaPlus" Zeta Potential Analyzer (Brookhaven Instrument Co.). The nanogel loading capacity with respect to insulin was ca. 0.25 to 0.3 mg/mg. Loaded nanogels III were condensed up to effective diameter 80 nm at the maximum insulin loading.

EXAMPLE 8

Blending of Nanogel with Polyethyleneimine

One percent aqueous solution of the polyethyleneimine, MW 50,000, (Aldrich) was prepared and filtered through 0.22 $\mu$m disposable filter. This solution was added dropwise to the nanogel III suspension prepared as described in the Example 6. This resulted in the condensation of loaded nanogel particles with the effective diameter of the particles reaching 110 nm as determined using "ZetaPlus" Zeta Potential Analyzer (Brookhaven Instrument Co.).

EXAMPLE 9

Cytotoxicity of Nanogels Particles

Cytotoxicity of free and oligonucleotide-loaded nanogel particles was determined using confluent KBv monolayers were grown in DMEM supplemented with 10% fetal bovine serum and 1 g/ml vinblastine. Cells were treated by nanogel II every 12 hours for 48 hours. After the treatment the cells were cultivated another 48 hours at 37° C. and 5% $CO_2$. After that, the drug cytotoxic activity was determined using the MTT (3-(4,5-dimethylthiazol-2-yl)2,5-diphenyl tetrazolium bromide) assay (Ferrari, et al., *J. Immunol. Methods* 131, 165, 1990). The results were as follows:

| Nanogel concentration, % | Cell survival, % |
|---|---|
| 2 | 20 |
| 0.2 | 50 |
| 0.02 | 80 |

What is claimed:

1. A polymer network comprising a plurality of cross-linked polymer fragments wherein the polymer fragments comprise:

(a) at least one polyanionic fragment which is an anionic homopolymer or copolymer comprising at least three repeating units, each of the repeating units is capable of ionization to form a negative charge in an aqueous solution; and (b) at least one nonionic homopolymer or copolymer comprising at least three of the same or different repeating units containing at least one atom selected from the group consisting of oxygen and nitrogen; wherein the polymer network is between about 20 nm and about 300 nm in size.

2. The polymer network of claim 1 wherein each of the repeating units in the polyanionic fragment are selected from the group consisting of oxygen, sulfur and phosphorous.

3. The polymer network of claim 1 wherein each of the repeating units in the polyanionic fragment is an acid selected from the group consisting of anionic amino acids, carboxylic, sulfonic, sulfuric, phosphoric and salts thereof.

4. The polymer network of claim 1 wherein each of the repeating units in the polyanionic fragment is selected from the group consisting of: polymethacrylic acid; polyacrylic acid; copolymers of methacrylic acids; copolymers of acrylic acid and salts thereof.

5. The polymer network of claim 1 wherein each of the repeating units in the polyanionic fragment is selected from the group consisting of: heparin; poly(phosphate); polyamino acid, polynucleotides, carboxylated dextran and copolymers thereof.

6. The polymer network of claim 1 wherein said polyanionic fragment comprises monomers selected from the group consisting of acrylic acid, aspartic acid, 1,4-phenylenediacrylic acid, citracinic acid, citraconic anhydride, trans-cinnamic acid, 4-hydroxy cinnamic acid, trans-glutaconic acid, glutamic acid, itaconic acid, linoleic acid, linolenic acid, methacrylic acid, trans-beta-hydromuconic acid, trans—trans-muconic acid, ricinolei acid, 2-propene-1-sulfonic acid, 4-styrene sulfonic acid, trans-traumatic acid, vinylsulfonic acid, vinyl phosphoric acid, vinyl benzoic acid and vinyl glycolic acid.

7. The polymer network according to claim 1 wherein the network size is between about 20 nm and about 200 nm.

8. The polymer network according to claim 1 wherein the network size is between about 20 nm and about 50 nm.

9. A composition comprising the polymer network of claim 1 and a biological agent.

10. The composition according to claim 9 wherein the biological agent is selected from the group consisting of polynucleotides, viral vectors, and viruses.

11. The composition according to claim 9 wherein the biological agent is selected from the group consisting of peptides and proteins.

12. The composition according to claim 9 wherein the biological agent is selected from the group consisting of immunoglobulins, immunomodulators, immunoadjuvants, immunogens, antigens, and vaccines.

13. The composition according to claim 9 wherein the biological agent is selected from the group consisting of dyes, radiolabels, radio-opaque compounds, and fluorescent compounds.

14. A pharmaceutical composition comprising the polymer network according to claim 1 and a pharmaceutically acceptable carrier.

15. A composition comprising the polymer network of claim 1 and a targeting molecule.

16. A method of immunizing an organism comprising administering to said organism an effective amount of a polymer network according to claim 1 and a biological agent.

17. A method of treating an organism in need of treatment comprising administering to said organism an effective amount of the polymer network composition of claim 1 and a biological agent.

18. The polymer network of claim 1 wherein the polyanionic and nonionic polymer fragments have a degree of polymerization between about 20 and about 100,000.

19. The polymer network of claim 18 wherein the degree of polymerization is between about 30 and about 10,000.

20. The polymer network of claim 19 wherein the degree of polymerization is between about 30 and 1,000.

21. The polymer network of claim 1 wherein the repeating units of the nonionic homopolymer or copolymer include at least one hydrophobic and at least one hydrophilic chain segment.

22. A polymer network comprising a plurality of cross-linked polymer fragments wherein the polymer fragments comprise:

(a) at least one polyanionic fragment which is an anionic homopolymer or copolymer comprising at least three repeating units, wherein each of the repeating units is selected from the group consisting of oxygen, sulfur and phosphorous and is capable of ionization to form a negative charge in an aqueous solution; and (b) at least one nonionic homopolymer or copolymer comprising at least three of the same or different nonionic repeating units containing at least one atom selected from the group consisting of oxygen and nitrogen; wherein the polymer network is between about 20 nm and about 300 nm in size.

* * * * *